(12) United States Patent
Park et al.

(10) Patent No.: US 8,735,439 B2
(45) Date of Patent: May 27, 2014

(54) CHLORIN E6-FOLIC ACID CONJUGATE, PREPARATION METHOD THEREOF, AND A PHARMACEUTICAL COMPOSITION FOR THE TREATMENT OF CANCER COMPRISING THE SAME

(75) Inventors: Kye Shin Park, Seoul (KR); Eun Hee Lee, Guri-si (KR); Hyo Jun Kim, Busan (KR)

(73) Assignee: Diatech Korea Co., Ltd., Seoul (KR)

( * ) Notice: Subject to any disclaimer, the term of this patent is extended or adjusted under 35 U.S.C. 154(b) by 1 day.

(21) Appl. No.: 12/594,186

(22) PCT Filed: Apr. 29, 2009

(86) PCT No.: PCT/KR2009/002276
§ 371 (c)(1),
(2), (4) Date: Jun. 23, 2011

(87) PCT Pub. No.: WO2010/126178
PCT Pub. Date: Nov. 4, 2010

(65) Prior Publication Data
US 2012/0059018 A1 Mar. 8, 2012

(51) Int. Cl.
*C07D 487/22* (2006.01)

(52) U.S. Cl.
USPC .......................................... 514/410; 540/145

(58) Field of Classification Search
USPC .......................................................... 540/145
See application file for complete search history.

(56) References Cited

FOREIGN PATENT DOCUMENTS

| KR | 1020010103763 A | 11/2001 |
|---|---|---|
| WO | 02/078694 A1 | 10/2002 |

OTHER PUBLICATIONS

Gravier, Julien, et al., Improvement of meta-tetra(Hydroxyphenyl)chlorin-Like Photosensitizer Selectivity with Folate-Based Targeted Delivery. Synthesis and in Vivo Delivery Studies, Journal of Medicinal Chemistry, 2008, vol. 51, No. 13, pp. 3867-3877.
Privalov, Valery A., et al., Five Years' Experience of Photodynamic Therapy with New Chlorin Photosensitizer, Proceedings of SPIE, 2005, vol. 5863, pp. 186-198.
Uzdensky, A.B., et al., Photodynamic effect of novel chlorin e6 derivatives on a single nerve cell, Life Sciences, 2004, vol. 74, pp. 2185-2197.
International Search Report dated Jan. 15, 2010 of PCT/KR2009/002276.
Notice of Allowance dated Sep. 7, 2009 of Korean Patent Application No. KR 10-2009-0037848.
Schneider R. et al, "Design synthesis and biological evaluation of folic acid targeted terraphenylporphyrin as novel photosensitizers for selective photodynamic therapy", Bioorganic Medicinal Chemistry, 2005, vol. 13 pp. 2799-2808.
Oseroff, A.R. et al "Antibody-targeted photolysis: Selective photodestruction of human T-cell leukemia cells using monoclonal antibody-chlorine6 conjugates", Proceedings of the National Academy of Sciences USA, 1986, vol. 83 pp. 8744-8748.
Hamblin, M.R. et al., "Pegylation of a Chlorin e6 Polymer Conjugate Increases Tumor Targeting of Photosensitizer", Cancer Research, Oct. 1, 2001, vol. 61, pp. 7155-7162.
Bachor, R. et al., "Photosensitized destruction of human bladder carcinoma cell treated with chlorin e6-conjugated microspheres", Proceedings of the National Academy of Sciences USA, Feb. 1991, vol. 88 pp. 1580-1584.
Akhlynina, T.V. et al., "Nuclear Targeting of Chlorin e6 Enhances Its Photosensitizing Activity", The Journal of Biological Chemistry, Aug. 15, 1997, vol. 272, No. 33, pp. 20328-20331.

*Primary Examiner* — Brian McDowell
(74) *Attorney, Agent, or Firm* — Cooley LLP

(57) ABSTRACT

The present invention relates to a novel chlorin e6-folic acid conjugate, a preparation method thereof, and a pharmaceutical composition for the treatment of cancer comprising the same, and more particularly, to a novel compound prepared by linking chlorin e6 to folic acid, which effectively produces singlet oxygen in various media and has much better tumor selectivity than the known porphyrin-based photosensitizers, thereby being used effectively in photodynamic therapy for malignant tumors, a preparation method thereof, and a pharmaceutical composition for photodynamic treatment of solid tumors comprising the compound as an active ingredient.

[Formula 1]

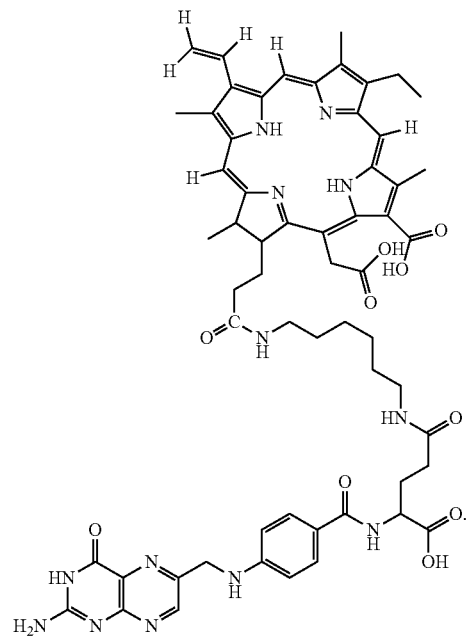

3 Claims, 10 Drawing Sheets

A

B

A

B

CHLORIN E6-FOLIC ACID CONJUGATE, PREPARATION METHOD THEREOF, AND A PHARMACEUTICAL COMPOSITION FOR THE TREATMENT OF CANCER COMPRISING THE SAME

This application is U.S. National Phase of International Application No. PCT/KR2009/002276, filed Apr. 29, 2009, designating the United States. The International Application was filed in the Korean language and has not been published as of the filing date of the present application. The Korean language application and its associated documents as originally filed in the International Application are hereby incorporated herein in their entirety.

TECHNICAL FIELD

The present invention relates to a novel chlorin e6-folic acid conjugate, a preparation method thereof, and a pharmaceutical composition for the treatment of cancer comprising the same, and more particularly, to a novel compound prepared by linking chlorin e6 to folic acid, which effectively produces singlet oxygen in various media and has much better tumor selectivity than the known porphyrin-based photosensitizers, thereby being used effectively in photodynamic treatment of malignant tumors, a preparation method thereof, and a pharmaceutical composition for photodynamic therapy of solid tumors comprising the compound as an active ingredient.

BACKGROUND ART

Photodynamic Therapy (hereinafter, referred to as PDT) has been widely introduced in clinical practice for the management of malignant tumors. One of the main factors specifying PDT efficiency is targetability or selectivity, which represents the extent of selective accumulation of photosensitizers only in tumor tissue, but not in healthy tissue. High targetability improves the efficiency of PDT to shorten the treatment period, and also to reduce the side effects of the drug that is introduced into the body. Activation of a photosensitizer by light at specific wavelengths leads to the production of reactive oxygen species such as singlet oxygen and radical species. The generated reactive oxygen species directly destroys tumor cells, and induces immune inflammatory responses and damage to the microvasculature of the tumor. Most photosensitizers tested accumulate with some selectivity in tumors, but they also concentrate in normal tissues, including the skin.

Targeted delivery of the photosensitizer could solve these problems through an enhanced photocytotoxicity as a result of higher and more selective accumulation in the tumor cells. Targeting implies conjugation of the photoactive compound to a tumor-seeking (specific) molecule, either directly or by the use of a carrier. Several photosensitizers have been already conjugated with antibodies directed against tumor-associated antigens. Ligands such as low-density lipoprotein, insulin, steroids, transferrin, and epidermal growth factor (EGF) have all been described for ligand-based targeting of photosensitizers to cells overexpressing the receptors for these ligands.

In fact, alterations in receptor expression, increased levels of specific cell surface membrane lipids and proteins as well as changes in the cellular microenvironment, all occur in diseased cells.

Among the different strategies for implementing receptor-mediated delivery systems, the receptor for folic acid also constitutes a useful target for tumor-specific drug delivery due to the following reasons.

(1) Folate receptors are upregulated in many human cancers, including malignancies of the ovary, colon, mammalian gland, and lung, and renal cell carcinoma, brain metastasis of epithelial tumor, and neuroendocrine carcinoma.

(2) Access to the folate receptor in normal tissues almost always does not occur since expression of the folate receptor in normal tissues can be severely limited due to its location on the apical membrane of polarized epithelia.

(3) The density of polarized epithelia and the folate receptor increases (the density of the folate receptor appears to increase as the stage/grade of the cancer worsens).

(4) Folate has a high affinity for its cell surface receptor. Conjugation of folic acid to macromolecules has been shown to enhance their delivery to folate receptor-expressing cancer cells in vitro in almost all situations tested.

Receptor of folic acid (RFA) is a glycosylphosphatidylinositol glycoprotein which binds with folic acid to facilitate folate uptake into cells via receptor-mediated endocytosis.

Although the precise mechanism of folate receptor transport of folic acid into cells via RFA remains unresolved, it is clear that folate conjugates are taken up nondestructively by mammalian cells via receptor-mediated endocytosis.

Physiologic folates move across the plasma membrane into the cytoplasm by a specialized endocytosis mediated pathway. After binding to folate receptor on the cancer cell surface, folate conjugates, regardless of size, are seen to absorb in intracellular compartments called endosomes.

Generally, the degree of selectivity or targetability does not exceed the ratio of 10:1 (cancer cell:normal cell). Accordingly, methods of selectively delivering the photosensitizer to the membrane receptor of specific cell groups by linking to the cell surface-specific vector ligand, such as antibodies, oligosaccharides, transferrin, and hormone analogs have been developed. Many studies reveal that conjugation of a chemotherapeutic agent with these vectors increases targeted delivery by 5-10 folds higher than non-conjugation. The cells are able to bind with the conjugate via receptor-mediated endocytosis without their destruction.

Folic acid consists of three components, and belongs to the class of vitamins.

Living organisms have mainly reduced into folic acid forms, such as dihydrofolic acid, tetrahydrofolic acid, and 5-methyl-tetrahydrofolic acid. They are cofactors for enzymes in which catalyze transportation of single carbon units. Folate-dependent enzymes participate in the biosynthesis of purine and pyrimidine nucleotides, and also in the metabolism of amino acids such as methionine, histidine, serine and glycine. Thus, folates are essential for cell division and growth.

After intake in vivo, folates are rapidly absorbed in blood and transported to tissues with blood plasma and erythrocytes.

Animal cells cannot synthesize folates. Hence, a specific system in the cell membrane for binding and absorption of folates is required.

As far as folic acid is a dianion with hydrophilic properties, it poorly penetrates through the cell plasma membrane by means of simple diffusion. Only at high pharmacological concentrations does passive diffusion contribute to folic acid transport.

Under natural physiological conditions, folic acid is available in the tissues and blood serum at nanomolar concentrations. That is why cells require a highly effective membrane system for absorption and transport of the vitamin.

A mobile carrier catalyzes folic acid transport at a high rate. The carrier is abundant in the epithelial cells of the small intestine, where folic acid absorption occurs. Catalyzed transport is the main route of folic acid absorption in various cells and a substrate of such transport is folic acid in restored form. For this reason, the carrier is called a transporter of restored vectors (TRV), which is a glycoprotein of 46 kD, forming a "channel" that permits hydrophilic molecules to pass through the cell membrane. The kinetics of TRV-mediated transport is described using Michaelis-Menten kinetics. The transport rate is rather high, and its affinity to folic acid is relatively low, about 200 μM.

TRV also operates in tumor cells. The affinity of restored folic acid, $K_M$ is in the range of 1-4 μM. The affinity of the carrier for methotrexate has a slightly lower $K_M$ in the range of 4-8 μM, and its maximum rate is in the range of 1-12 nmol/min per cellular protein (g). TRV functions in the folate transport across cell membranes, but its affinity for oxygenated folic acid is low ($K_M$ is in the range of 100-200 μM).

A receptor-mediated system functions through a membrane glycoprotein called a folate receptor. A folate receptor is very similar to substrata in that its association constant for folate is less than 1 nM.

The receptor-mediated transport of folic acid takes place in one direction, namely, to take folate into cells. Normal cells express very few folate receptors on their surfaces, although with some exceptions. However, high levels of folate receptor on the cell surface are observed in malignant transformed cells, in particular, tumor cells in the lung, kidney, brain, large intestine, and ovary, and myelocytic blood cells in leukemia. Due to the increase in its quantity, folate receptors are more efficiently capable of binding with a significant amount of folic acid (more than $6 \cdot 10^7$ molecules per cell). As far as it is shown that monoclonal antibodies used for cancer diagnostic purposes bind with folic acid with high specificity, such glycoprotein could be referred to as a tumor marker.

The receptor-mediated transport of folic acid is driven by endocytosis. The receptor operates through a recirculatory mechanism. That is, while a ligand repeats binding and release of molecules, the molecules are transported across the plasma membrane into endosomes, and in the opposite direction. Efficiency of this function is specified by various factors as follows: the number of receptors on the cell surface, extracellular concentration of folic acid-ligand, affinity of folate for receptor, the rate of energy-dependent endocytosis, the release rate of receptor molecules from endosome, and the capability of the receptor to be repeatedly reintegrated into the membrane, etc.

A folate receptor-associated fraction in folate-drug conjugates will traffic into the cells by receptor-mediated endocytosis, while the remainder will remain on the cell surfaces. In this regard, two types of therapeutic strategies can be envisioned. Drugs that require access to intracellular targets can be delivered in substantial quantities to cytosolic locations by the endocytic pathway, while drugs that can or must function at an extracellular location will be enriched on cancer cell surfaces by the stationary population of the folate receptor.

An important feature is the direct delivery of the drug to pathologically transformed cells. The therapeutic effect of PDT using a number of photosensitizers is mediated by changing the physiological conditions of the pathological focus, but not by direct damage to tumor cells. Thus, hydrophilic pigments, in particular, chlorin e6 cause photodamage to the vascular system of tumor tissue (the effect of PDT to blood vessel), which inhibits tumor growth without direct inactivation of the transformed cells. It is apparent that selective delivery of photosensitizers to tumors could be one of the ways to improve the therapeutic effects of PDT.

Chlorin e6 is a natural compound, and non-toxic to normal cells of organisms. It also has higher photochemical activity on malignant cells than other photoactive compounds used in tumor therapy.

Chlorin e6 drugs quickly proceed from blood and organs to tumor affected areas, and accumulate in tumor cells at high therapeutic concentrations.

Laser-activated chlorin e6 directly destroys tumor cells as well as having indirect specific anti-tumor immunomodulating effect at the cost of cell immunity. High accumulations of chlorin e6 in the inflammatory foci or regenerating tissues provides better healing of post-operative wounds and prevents reinfection.

DISCLOSURE

Technical Problem

Accordingly, in consideration of the above mentioned facts, the present inventors have prepared a novel chlorin e6-folic acid conjugate that is prepared by linking chlorin e6 to folic acid via hexane-1,6-diamine as a linker, which effectively produces singlet oxygen in various media and has much better tumor selectivity than the known porphyrin-based photosensitizers, thereby being useful in photodynamic treatment of malignant tumors. They found that the compound has excellent tumor selectivity compared to the known porphyrin-based photosensitizers, and thus can be effectively used in photodynamic treatment of malignant tumors, thereby completing the present invention.

Technical Solution

It is an object of the present invention to provide a novel chlorin e6-folic acid conjugate that has much better tumor selectivity than the known porphyrin-based photosensitizers, thereby being used in photodynamic treatment of malignant tumors.

It is another object of the present invention to provide a method for preparing the novel chlorin e6-folic acid conjugate by linking chlorin e6 to folic acid via hexane-1,6-diamine or 2,2'-ethylenedioxy-bis-ethylamine as a linker.

It is still another object of the present invention to provide a pharmaceutical composition for photodynamic treatment of solid tumors, comprising the novel chlorin e6-folic acid conjugate as an active ingredient.

Advantageous Effects

The present invention provides a novel chlorin e6-folic acid conjugate, [γ-(6-aminohexyl)folic acid]-chlorin e6 that is prepared by linking chlorin e6 to folic acid via hexane-1, 6-diamine as a linker, which effectively produces singlet oxygen in various media and has much better tumor selectivity than the known porphyrin-based photosensitizers, thereby being effectively used in photodynamic treatment of malignant tumors; a preparation method thereof; and a pharmaceutical composition for the treatment of cancer comprising the same.

BEST MODE

Figure 1:
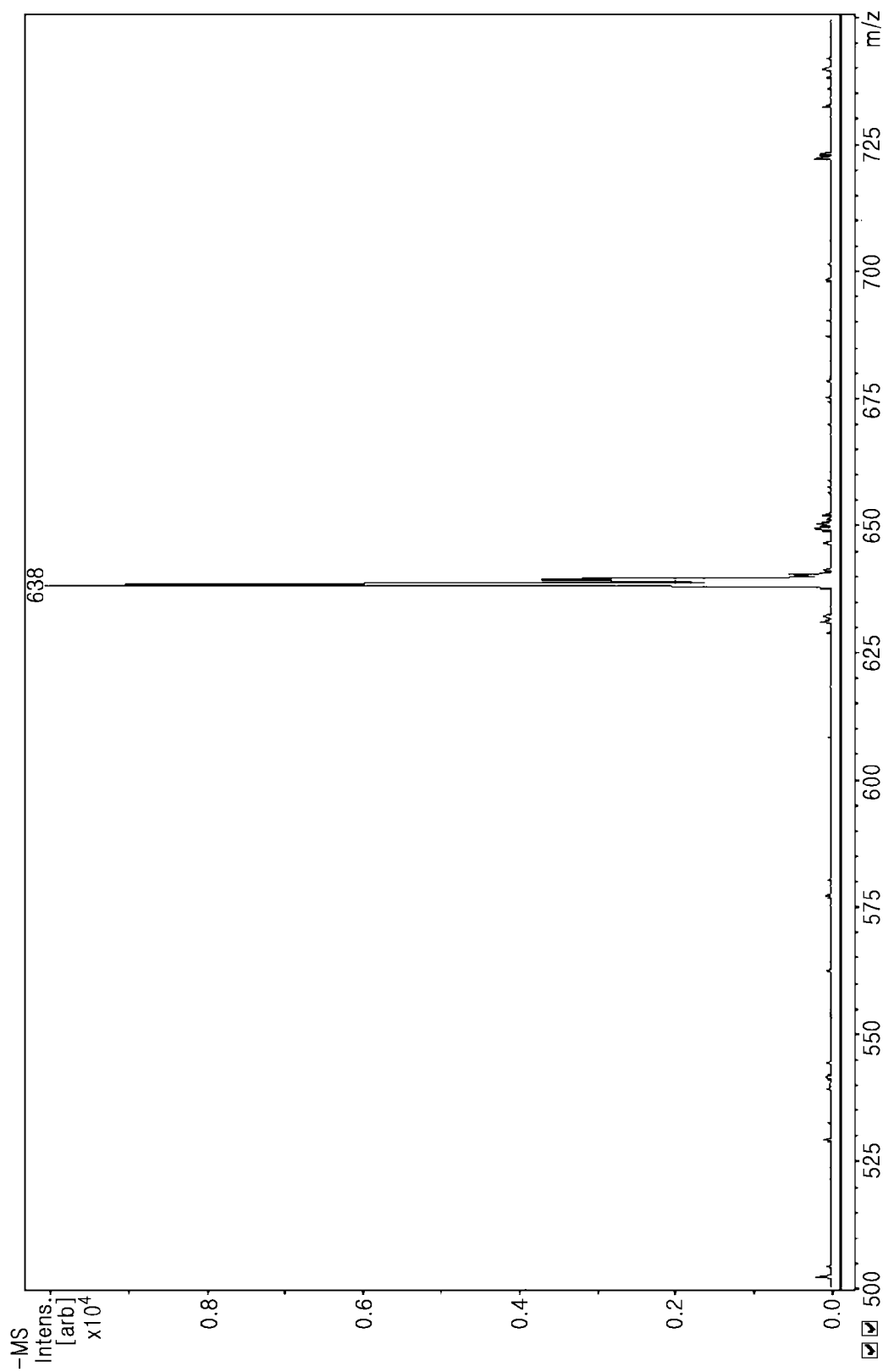
FIG. 1 is the result of mass spectrometry (negative mode) of γ-{[tert-butyl-N-(6-aminohexyl)]carbamate}folic acid.

In one aspect, the present invention provides a novel chlorin e6-folic acid conjugate, [γ-(6-aminohexyl)folic acid]-chlorin e6 or {γ-{N-{2-[2-(2-aminoethoxy)ethoxy]ethyl}folic acid}}-chlorin e6, which is represented by the following Formula 1 or 2, or a pharmaceutically acceptable salt thereof.

[Formula 1]

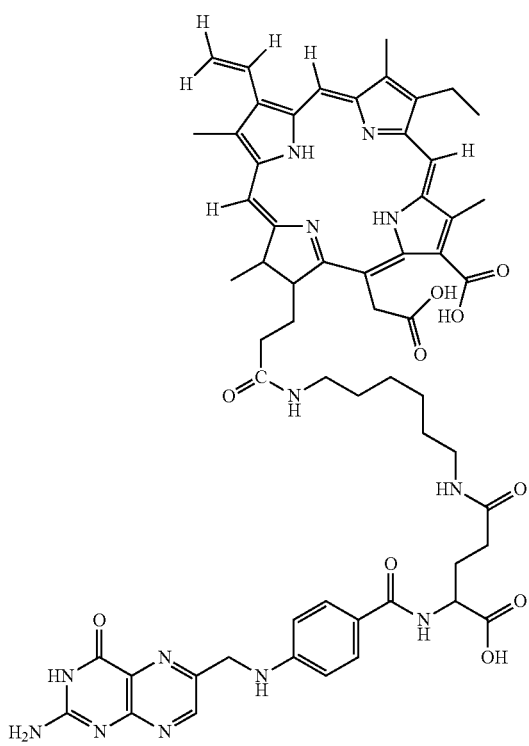

[Formula 2]

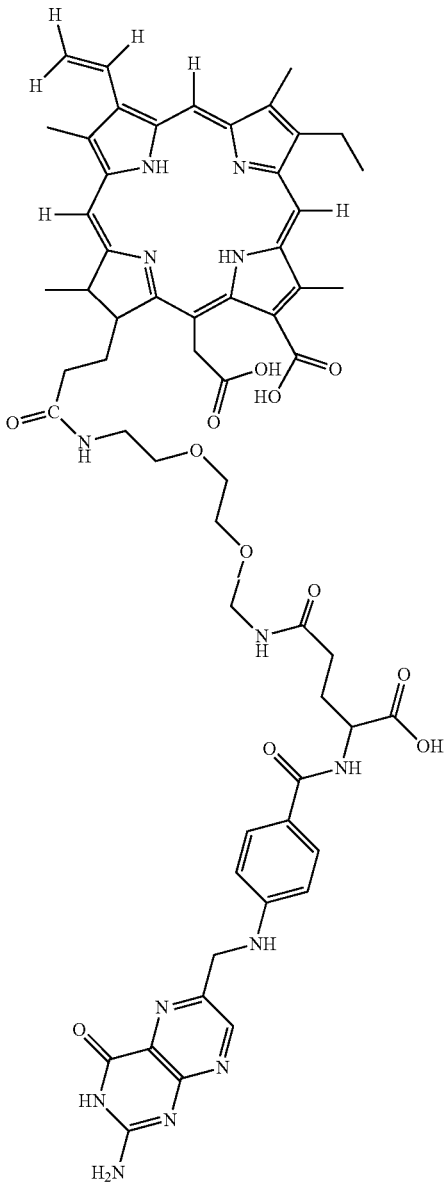

In another aspect, the present invention provides a method for preparing a novel chlorin e6-folic acid conjugate, [γ-(6-aminohexyl)folic acid]-chlorin e6 or {γ-{N-{2-[2-(2-aminoethoxy)ethoxy]ethyl}folic acid}}-chlorin e6, which is represented by the following Formula 1 or 2, or a pharmaceutically acceptable salt thereof, comprising the steps of:

reacting folic acid with [tert-butyl-N-(6-aminohexyl)]carbamate or tert-butyl 2-(2-(2-aminoethoxy)ethoxy)ethylcarbamate under a nitrogen atmosphere at room temperature to obtain γ-{[tert-butyl-N-(6-aminohexyl)]carbamate}folic acid or γ-{N-{2-[2-(2-aminoethoxy)ethoxy]ethyl carbamate}folic acid;

treating γ-{[tert-butyl-N-(6-aminohexyl)]carbamate}folic acid or γ-{N-{2-[2-(2-aminoethoxy)ethoxy]ethyl carbamate}folic acid of the above step with trifluoro-acetic acid to obtain γ-(6-aminohexyl)folic acid or γ-{N-{2-[2-(2-aminoethoxy)ethoxy]ethyl}}folic acid;

adding N-hydroxysuccinimide and dicyclohexylcarbodiimide, in the dark under a nitrogen atmosphere, to chlorin e6 to obtain chlorin e6 succinidyl ester; and adding chlorin e6 succinidyl ester to the prepared γ-(6-aminohexyl)folic acid or γ-{N-{2-[2-(2-aminoethoxy)ethoxy]ethyl}}folic acid in the dark under a nitrogen atmosphere, to prepare [γ-(6-aminohexyl)folic acid]-chlorin e6 or {γ-{N-{2-[2-(2-aminoethoxy)ethoxy]ethyl}folic acid}}-chlorin e6.

[Formula 1]

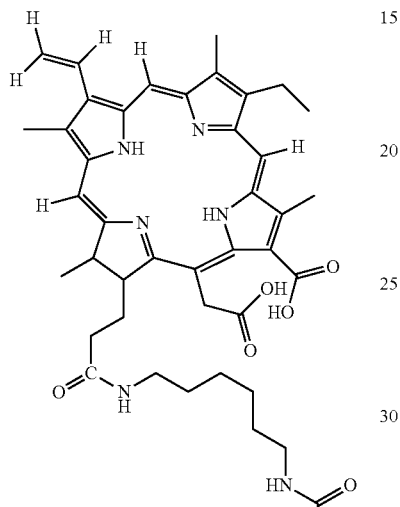

-continued

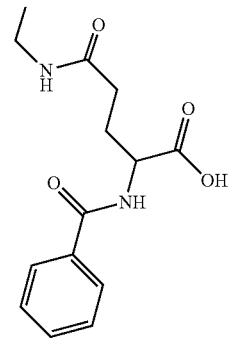

In still another aspect, the present invention provides a pharmaceutical composition for photodynamic treatment of solid tumors, comprising the novel chlorin e6-folic acid conjugate, [γ-(6-aminohexyl)folic acid]-chlorin e6 or {γ-{N-{2-[2-(2-aminoethoxy)ethoxy]ethyl}folic acid}}-chlorin e6, which is represented by the following Formula 1 or 2, or a pharmaceutically acceptable salt thereof as an active ingredient.

[Formula 1]

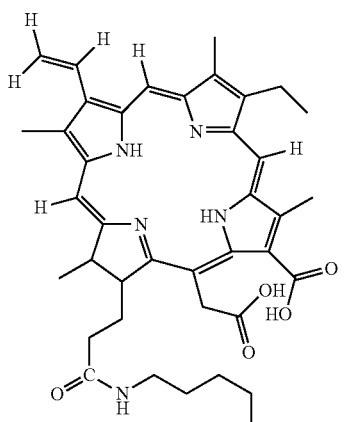

[Formula 2]

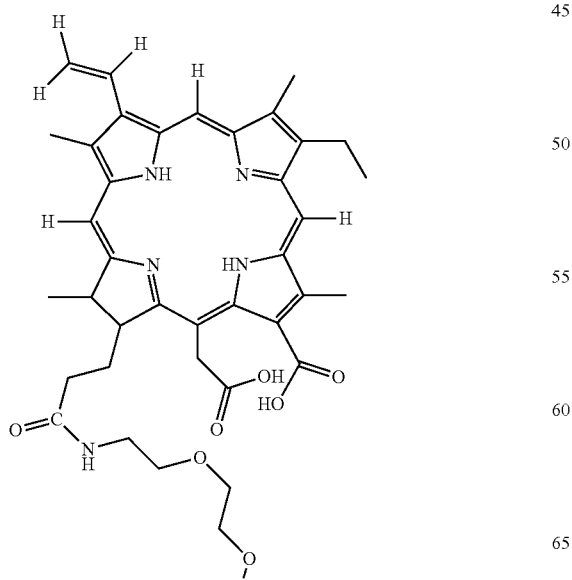

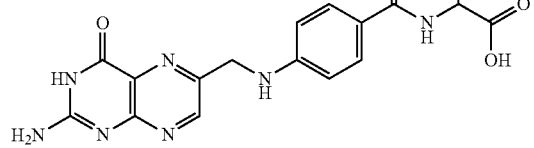

-continued

[Formula 2]

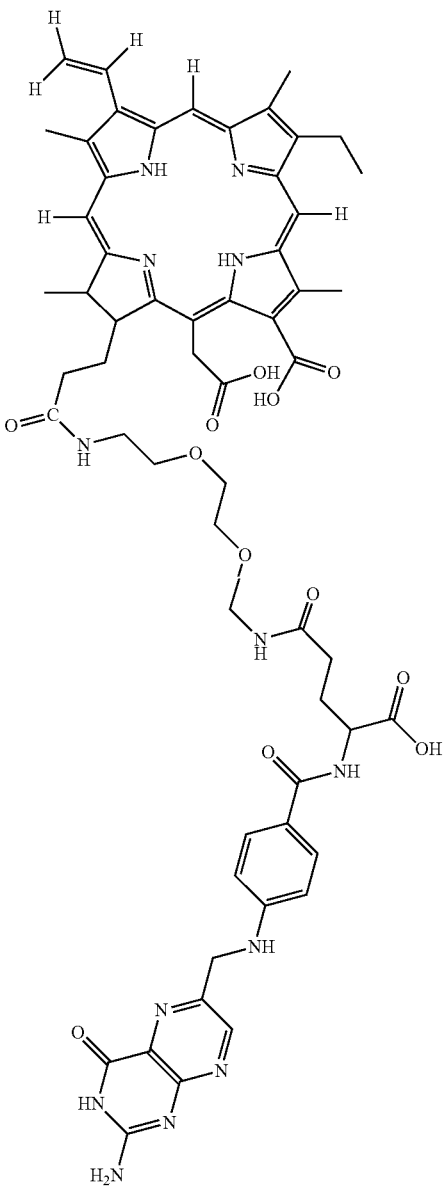

Hereinafter, the present invention will be described in detail.

As used herein, the term "cancer" refers to complex diseases resulting from unrestrained proliferation and uncontrolled growth of transformed cells. In the present invention, this means solid tumors to be treated by photodynamic therapy. Solid tumors connote cancer of body tissues other than the blood. Examples of solid tumor include brain tumor, low-grade astrocytoma, high-grade astrocytoma, pituitary adenoma, meningioma, CNS lymphoma, oligodendroglioma, craniopharyngioma, ependymoma, brain stem tumor, head and neck tumor, larygeal cancer, oropgaryngeal cancer, nasal cavity/PNS tumor, nasopharyngeal tumor, salivary gland tumor, hypopharyngeal cancer, thyroid cancer, oral cavity tumor, chest tumor, small cell lung cancer, non-small cell lung cancer (NSCLC), thymoma, mediastinal tumor, esophageal cancer, breast cancer, male breast cancer, abdomen-pelvis tumor, stomach cancer, hepatoma, gall bladder cancer, billiary tract tumor, pancreatic cancer, small intestinal tumor, large intestinal tumor, anal cancer, bladder cancer, renal cell carcinoma, prostatic cancer, cervix cancer, endometrial cancer, ovarian cancer, uterine sarcoma, and skin cancer.

The compound of Formula 1 or 2 of the present invention may be prepared in the form of a pharmaceutically acceptable salt and a solvate according to the conventional method in the related art.

As the pharmaceutically acceptable salt, acid addition salts produced with free acids are preferred. The acid addition salts are prepared by the conventional method, for example, by dissolving the compound in an excessive amount of acid aqueous solution, and then precipitating the salt using a water-miscible organic solvent such as methanol, ethanol, acetone or acetonitrile. Acid or alcohol (For example, glycol monomethyl ether) in the equal molar amount of the compound and water is heated, and the mixture is dried by evaporation or the precipitated salt can be suction-filtered.

At this time, as the free acids, organic acids and inorganic acids may be used. Examples of the inorganic acids include hydrochloric acid, phosphoric acid, sulfuric acid, nitric acid, and tartaric acid, and examples of the organic acids include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutaric acid, glucuronic acid, aspartic acid, ascorbic acid, carbonic acid, vanillic acid, and hydroiodic acid, but are not limited thereto.

Further, a pharmaceutically acceptable metal salt can be prepared using a base. An alkali metal salt or alkaline earth metal salt can be obtained by a method, for example, by dissolving a compound in an excessive amount of alkali metal hydroxide or alkaline earth metal hydroxide solution, filtering the undissolved salt, and then evaporating and drying the filtrate. In respect to metal salts, sodium, potassium, or calcium salt is pharmaceutically preferable, but is not limited thereto. The corresponding silver salt can be obtained by reacting alkali metal salt or alkaline earth metal salt with a suitable silver salt (e.g. silver nitrate).

A pharmaceutically acceptable salt of the compound represented by Formula 1 or 2 includes salts of acidic or basic groups, which can be present in the compound of Formula 1 or 2, unless otherwise specifically indicated. For example, the pharmaceutically acceptable salt includes sodium salt, calcium salt, and potassium salt of hydroxy group, and other pharmaceutically acceptable salt of amino group includes hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate). Further, the salts can be prepared by a preparation method known in the related art.

In the present invention, the folic acid and the chlorin e6 are attached to the distal ends of two linkers in order to increase the range of accessible receptor sites. For the linkage between two linkers, hexane-1,6-diamine or 2,2'-(ethylenedioxy)-bis-ethylamine is used.

That is, the novel chlorin e6-folic acid conjugate of the present invention, {γ-{N-{2-[2-(2-aminoethoxy)ethoxy]ethyl}folic acid}}-chlorin e6 or a pharmaceutically acceptable salt thereof can be prepared by linking chlorin e6 (13-carboxy-17-[2-carboxyethyl]-15-carboxymethyl-17,18-trans-dihydro-3-vinyl-8-ethyl-2,7,12,18-tetramethylporphyrin) of the following Formula 3 with folic acid (N-[4(2-Amino-4-hydroxy pteridin-6-ylmethylamino) benzoyl]-L(+)-glutamic acid) of the following Formula 4 via hexane-1,6-diamine or via 2,2'-(ethylenedioxy)-bis-ethylamine, to thereby obtain the compound of Formula 1 or 2, respectively.

[Formula 3]

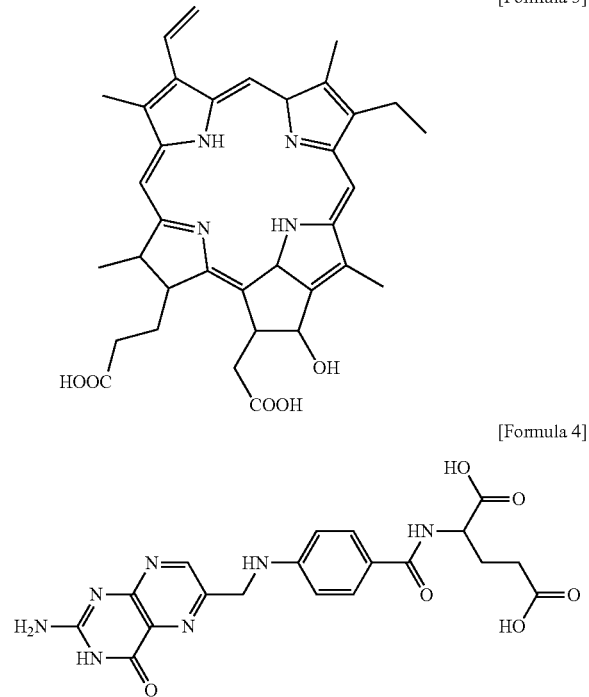

[Formula 4]

In one preferred aspect, the novel chlorin e6-folic acid conjugate having the structure of Formula 1, namely, [γ-(6-aminohexyl)folic acid]-chlorin E6 or a pharmaceutically acceptable salt thereof can be prepared by the method comprising the following steps:

reacting folic acid with [tert-butyl-N-(6-aminohexyl)]carbamate under a nitrogen atmosphere at room temperature to obtain γ-{(tert-butyl-N-(6-aminohexyl)]carbamate}folic acid;

treating γ-{[tert-butyl-N-(6-aminohexyl)]carbamate}folic acid of the above step with trifluoro-acetic acid to obtain γ-(6-aminohexyl)folic acid;

adding N-hydroxysuccinimide and dicyclohexylcarbodiimide in the dark under a nitrogen atmosphere to chlorin E6 to obtain chlorin E6 succinidyl ester; and adding chlorin E6 succinidyl ester to the prepared γ-(6-aminohexyl)folic acid in the dark under a nitrogen atmosphere to prepare [γ-(6-aminohexyl)folic acid]-chlorin E6.

In another preferred aspect, the novel chlorin e6-folic acid conjugate having the structure of Formula 2, namely, {γ-{N-{2-[2-(2-aminoethoxy)ethoxy]ethyl}folic acid}}-chlorin e6 or a pharmaceutically acceptable salt thereof can be prepared by the method comprising the following steps:

reacting folic acid with tert-butyl 2-(2-(2-aminoethoxy)ethoxy)ethylcarbamate under a nitrogen atmosphere at room temperature to obtain γ-{N-{2-[2-(2-aminoethoxy)ethoxy]ethyl carbamate}folic acid};

treating γ-{N-{2-[2-(2-aminoethoxy)ethoxy]ethyl carbamate}folic acid of the above step with trifluoro-acetic acid to obtain γ-{N-{2-[2-(2-aminoethoxy)ethoxy]ethyl}}folic acid;

adding N-hydroxysuccinimide and dicyclohexylcarbodiimide in the dark under a nitrogen atmosphere to chlorin e6 to obtain chlorin e6 succinidyl ester; and adding chlorin e6 succinidyl ester in the dark under a nitrogen atmosphere to the prepared γ-{N-{2-[2-(2-aminoethoxy)ethoxy]ethyl}}folic acid to prepare {γ-{N-{2-[2-(2-aminoethoxy)ethoxy]ethyl}folic acid}}-chlorin e6.

Specifically, the step of obtaining γ-{[tert-butyl-N-(6-aminohexyl)]carbamate}folic acid can be performed as follows:

a solution of folic acid in anhydrous DMSO and pyridine are added under a nitrogen atmosphere at room temperature, to tert-butyl-N-(6-aminohexyl)]carbamate and dicyclohexylcarbodiimide, and the mixture is stirred for 10~30 hrs. After filtration of the reaction mixture, the filtrate is gradually poured into a vigorously stirred solution of anhydrous Et₂O cooled to 0° C. to obtain a yellow precipitate. The precipitate is filtered, collected, and washed with EtO to remove DMSO residue, and then dried under high vacuum.

Specifically, the step of obtaining γ-{N-{2-[2-(2-aminoethoxy)ethoxy]ethyl carbamate}folic acid can be performed as follows.

a solution of folic acid in anhydrous DMSO and pyridine is added to 2,2'-(ethylenedioxy)-bis-ethylamine and dicyclohexylcarbodiimide under a nitrogen atmosphere at room temperature and the mixture is stirred for 10~30 hrs. After filtration of the reaction mixture, the filtrate is gradually poured into a vigorously stirred solution of anhydrous Et₂O cooled to 0° C. to obtain a yellow precipitate, is the precipitate is filtered, collected, and washed with EtO to remove DMSO residue, and then dried under high vacuum.

Specifically, the step of obtaining γ-(6-aminohexyl)folic acid or γ-{N-{2-[2-(2-aminoethoxy)ethoxy]ethyl}}folic acid can be performed as follows.

The γ-{[tert-butyl-N-(6-aminohexyl)]carbamate}folic acid or γ-{N-{2-[2-(2-aminoethoxy)ethoxy]ethyl carbamate}folic acid prepared as above is treated with trifluoroacetic acid (TFA), and stirred at ambient temperature for 1~5 hrs. TFA is evaporated under vacuum and the residue is taken up in anhydrous DMF. Pyridine is added dropwise until complete formation of a yellow precipitate, which is collected by filtration, washed with Et₂O and dried under vacuum.

Specifically, the step of obtaining chlorin e6 succinidyl ester can be performed as follows:

a solution of chlorin e6 in anhydrous DMSO are to added N-hydroxysuccinimide and dicyclohexylcarbodiimide In the dark under a nitrogen atmosphere. The mixture is stirred for 2~6 hrs at room temperature. The solvent is evaporated and the raw material is purified by column chromatography using a mixed solvent of acetone:CH₂Cl₂ (1:9 (v/v)) as the eluent. The fractions are tested by TLC, those containing only one single spot are collected and concentrated.

Specifically, the step of preparing [γ-(6-aminohexyl)folic acid]-chlorin e6 or {γ-{N-{2-[2-(2-aminoethoxy)ethoxy]ethyl}folic acid}}-chlorin e6 can be performed as follows:

Chlorin e6 succinidyl ester is added to a solution of γ-(6-aminohexyl)folic acid or γ-{N-{2-[2-(2-aminoethoxy)ethoxy]ethyl}}folic acid, in the dark under a nitrogen atmosphere, in anhydrous DMSO and pyridine, and the mixture is stirred at room temperature for 12~48 hrs. The mixture is gradually poured into a vigorously stirred solution of Et₂O cooled to 0° C. The dark red precipitate obtained is filtered, collected, and washed with Et₂O and CH₂Cl₂, and then dried under vacuum.

To confirm whether folic acid in the content of obtained chlorine e6-folic acid conjugate completely preserves its receptor features, electronic absorption spectrometry and fluorescence spectrometry were performed. In the electronic absorption spectra, the specific maximum for chlorin appeared at 400 and 650 nm, and the specific maximum for folic acid appeared at 270 nm with the shoulder at 360 nm. In the fluorescence spectra of the conjugate, the maximum corresponding to chlorin appeared at 660 nm and 700 nm, and the specific maximum for folic acid appeared at 445 nm.

Further, the efficiency of singlet oxygen production of the novel chlorin e6-folic acid conjugate of the present invention was evaluated in homogeneous and heterogeneous systems. Consequently, it was confirmed that the chlorin e6-folic acid conjugate of the present invention has optimal characteristics for effective generation of singlet oxygen in different media. Considering its unique tropism to tumor cells and tissues, it can be seen that the chlorin e6-folic acid conjugate of the present invention has much higher photodynamic activity than all currently known porphyrin-based photosensitizers.

Furthermore, to examine in vitro biological effects of the novel chlorin e6-folic acid conjugate of the present invention, Hela cells, which are one of the numerous tumor cell types that overexpress folate receptors, were used to examine the intracellular accumulation and targeted delivery of the photoactive compound. It was found that after 24 hrs incubation, the intracellular accumulation of chlorin e6-folic acid conjugate was on average about 10-fold higher than chlorin e6.

Lastly, to examine in vivo biological effects of the novel chlorin e6-folic acid conjugate of the present invention, lifetime laser fluorescence spectroscopy was performed to examine the accumulation of chlorin e6 and chlorin e6-folic acid conjugate. In the tumor tissues of rats with sarcoma M-1, the maximum accumulation of chlorin e6 was observed for nearly 5 hrs after intravenous administration of 10.0 mg/kg. The maximum accumulation of chlorin e6 conjugate was observed for 2-5 hrs after administration of 5.0 mg/kg. PDT was performed using the chlorin e6-folic acid conjugate at a dose of 2.5, 5.0 and 10.0 mg/kg, and its antitumor effects were evaluated by measuring the necrotic area formed in sarcoma M-1. When the chlorin e6-folic acid conjugate was administered at a dose of 10.0 mg/kg, excellent effects were observed, in which the necrosis ratio was 66.16%. The inhibitory effects on tumor volumetric growth in rats with sarcoma M-1 were monitored for 24 days after PDT using the chlorin e6-folic acid conjugate. Compared to the control group, it showed the inhibition rate of 86.34%~99.1%.

These results indicate that the chlorin e6-folic acid conjugate has strong affinity for tumor cells and cell membrane. These accumulation assays in sarcoma suggested that the chlorin e6-folic acid conjugate has much higher tumor tropism than chlorin e6. Therefore, in photodynamic therapy, the chlorin e6-folic acid conjugate provides more excellent efficiency than chlorin e6.

Therefore, the novel chlorin e6-folic acid conjugate of the present invention has excellent tumor selectivity compared to the known porphyrin-based photosensitizers, thereby being used in photodynamic therapy for malignant tumors.

The composition of the present invention may further comprise one or more active ingredients having the same as or similar function to that of [γ-(6-aminohexyl)folic acid]-chlorin e6 or {γ-{N-{2-[2-(2-aminoethoxy)ethoxy]ethyl}folic acid}}-chlorin e6, or a pharmaceutically acceptable salt thereof.

For administration, the composition of the present invention may be prepared by including at least one pharmaceutically acceptable carrier, in addition to the active ingredients as described above. Examples of the pharmaceutically acceptable carrier include saline solution, sterile water, Ringer's solution, buffered saline solution, dextrose solution, maltodextrin solution, glycerol, ethanol and a mixture of one or more thereof. If necessary, the composition may also contain other conventional additives, such as antioxidants, buffers, and bacteriostatic agents. Moreover, the composition may additionally contain diluents, dispersants, surfactants, binders, and lubricants in order to formulate it into injectable formulations, such as aqueous solution, suspension, emulsion, pills, capsules, granules and tablets. Furthermore, the composition may preferably be formulated depending on particular diseases and its components, using the method described in Remington's Pharmaceutical Science (latest edition), Mack Publishing Company, Easton Pa., which is a suitable method in the relevant field of art.

The composition of the present invention may be administered orally or parenterally (for example, intravein, subcutaneous, intraperitoneal, or topical application) depending on the purpose of the present invention, and the dosage of the composition can vary depending on various factors, including patient's weight, age, sex, health condition, and diet, and administration time, administration route, secretion rate, disease severity, etc. The chlorin e6-folic acid conjugate of the present invention is administered at a daily dosage of about 5 to 1000 mg/kg, preferably 10 to 500 mg/kg, once or several times.

The composition of the present invention may be used alone or in combination with surgical operations, hormone therapies, chemical therapies, and other methods using biological reaction regulators in order to treat solid tumors.

MODE FOR INVENTION

Hereinafter, the present invention will be described in more detail with reference to Examples. However, these Examples are for illustrative purposes only, and the invention is not intended to be limited by these Examples.

Example 1-1 (Compound I)

Synthesis of γ-{[tert-butyl-N-(6-aminohexyl)]carbamate}folic acid (I)

To a solution of folic acid (1615 mg, 3.66 mmol) in anhydrous DMSO and pyridine were added [tert-butyl-N-(6-aminohexyl)]carbamate(=N-boc-1,6-hexanediamine) (871 mg, 4.03 mmol) and dicyclohexylcarbodiimide (DCC) (1887 mg, 9.15 mmol) (or 1,1'-carbonyldiimidazole) under a nitrogen atmosphere at room temperature, and the mixture was stirred for 18 hrs at room temperature. The reaction mixture was filtered and the filtrate was gradually poured into a vigorously stirred solution of anhydrous $Et_2O$ cooled to 0° C. The yellow precipitate was collected by filtration, washed with EtO after isolation to remove trace amounts of DMSO and dried under vacuum to obtain 2132 mg of compound (yield: 91.0%).

The mass spectrometry (negative mode) of γ-{[tert-butyl-N-(6-aminohexyl)]carbamate}folic acid showed that the molecular weight was 639.73 (FIG. 1).

Example 1-2 (Compound I-I)

Synthesis of γ-{N-{2-[2-(2-aminoethoxy)ethoxy]ethyl carbamate}folic acid

A solution of folic acid (3.66 mmol) in anhydrous DMSO and pyridine were added to tert-butyl 2-(2-(2-aminoethoxy)ethoxy)ethylcarbamate (4.03 mmol) and dicyclohexylcarbodiimide (DCC) (9.15 mmol) (or 1,1'-carbonyldiimidazole) under a nitrogen atmosphere at room temperature, and the mixture was stirred for 18 hrs at room temperature. The reaction mixture was filtered and the filtrate was gradually poured into a vigorously stirred solution of anhydrous $Et_2O$ cooled to 0° C. The yellow precipitate was collected by filtration, washed with EtO after isolation to remove trace amounts of DMSO and dried under vacuum.

Example 2

Synthesis of γ-(6-aminohexyl)folic acid (II)

Compound I (2232 mg, 3.49 mmol) prepared in Example 1-1 or Compound I-I (3.49 mmol) prepared in Example 1-2 was treated with trifluoroacetic acid (TFA). After stirring at ambient temperature for 2 hrs, TFA was evaporated under vacuum and the residue was taken up in anhydrous DMF. Pyridine was added dropwise until complete formation of a yellow precipitate, which was collected by filtration, washed with $Et_2O$ and dried under high vacuum to yield the product II or II-I, respectively. Compound I was used as a starting material to obtain 1652 mg of product (Compound II) (yield: 87.9%).

Figure 2:
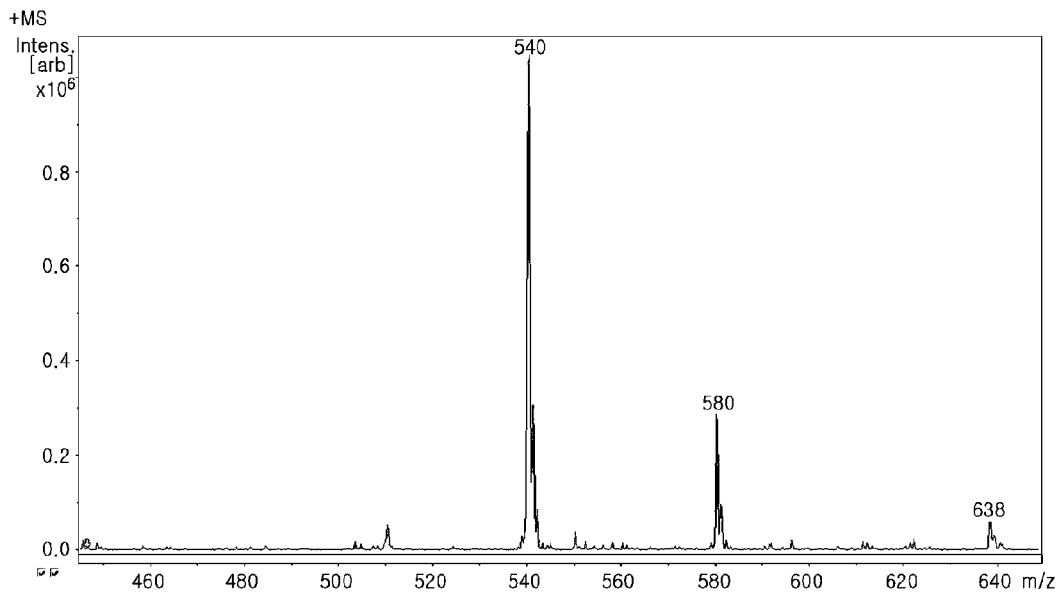
FIG. 2 is the result of mass spectrometry of γ-(6-aminohexyl)folic acid, in which A is the result in the positive mode and B is the result in the negative mode.
Figure 2:
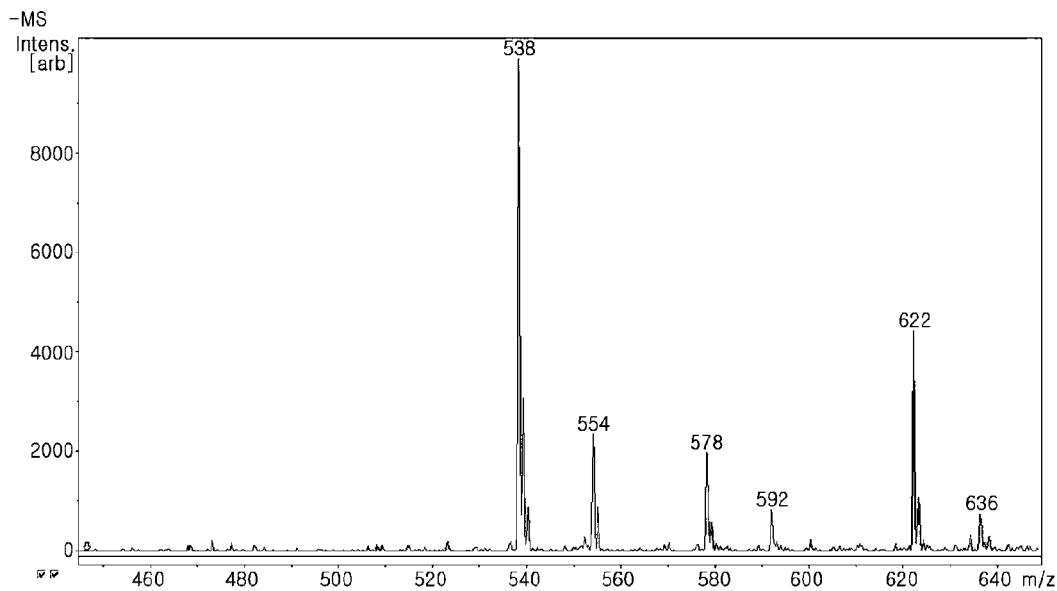

The mass spectrometry of the product (compound II) γ-(6-aminohexyl)folic acid showed that the molecular weight was 538.79 (FIG. 2). In FIG. 2, A is the result in the positive mode, and B is the result in the negative mode.

Example 3

Synthesis of Chlorin $e_6$ Succinidyl Ester (III)

a solution of chlorin e6 (45.37 mg, $7.6 \times 10^{-2}$ mmol) in anhydrous DMSO was added to N-hydroxysuccinimide (8.7 mg, $7.6 \times 10^{-2}$ mmol) and dicyclohexylcarbodiimide (DCC) (8.7 mg, $7.6 \times 10^{-2}$ mmol) In the dark under a nitrogen atmosphere. The mixture was stirred for 4 hrs at room temperature. The solvent was evaporated and the raw material purified by column chromatography using acetone:$CH_2Cl_2$ (1:9 (v/v)) as the eluent. The fractions were tested by TLC, those containing only one single spot were collected and concentrated, so as to obtain 42 mg (yield: 79.7%).

Figure 3:
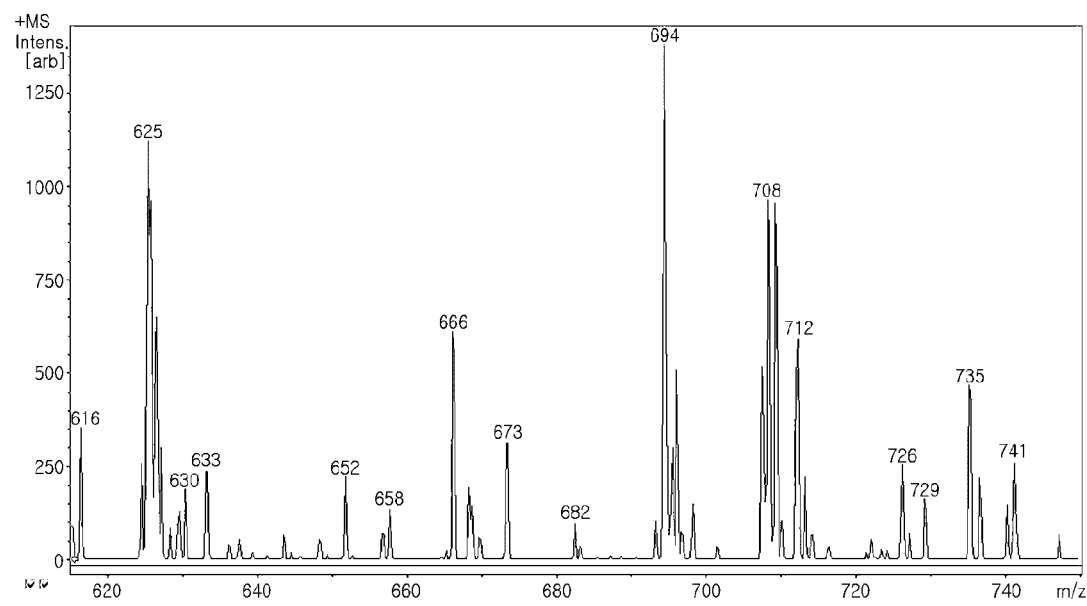
FIG. 3 is the result of mass spectrometry of chlorin $e_6$ succinidyl ester, in which A is the result in the positive mode and B is the result in the negative mode.
Figure 3:
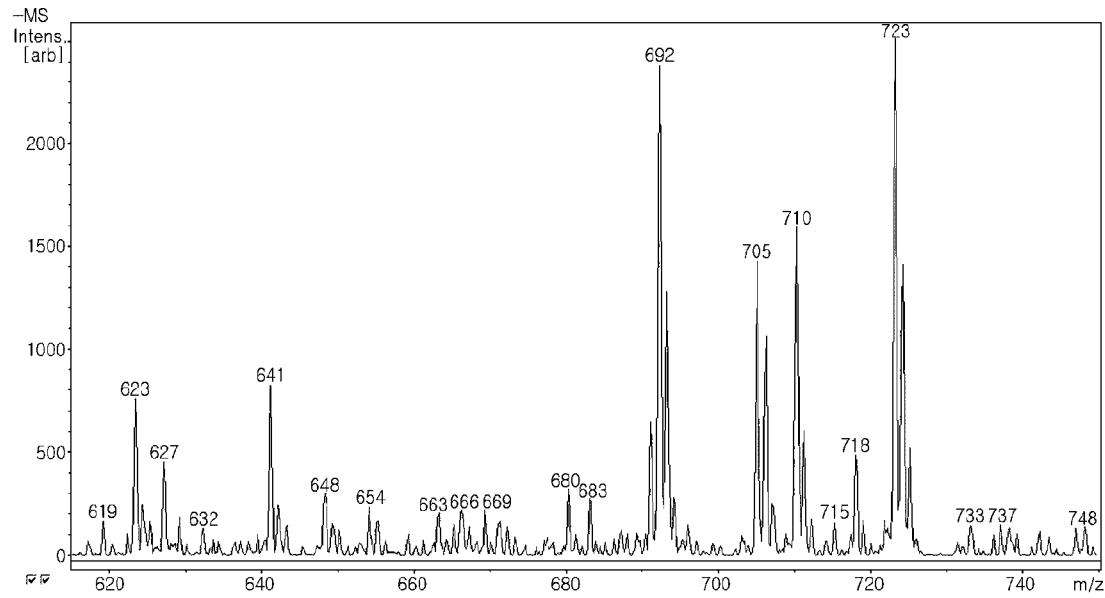

The mass spectrometry of chlorin $e_6$ succinidyl ester showed that the molecular weight was 693.74 (FIG. 3). In FIG. 3, A is the result in the positive mode, and B is the result in the negative mode.

Example 4

Synthesis of [γ-(6-aminohexyl)folic acid]-chlorin $e_6$ (IV)

A solution of Compound II (29.3 mg, $5.45 \times 10^{-2}$ mmol) or Compound II-I ($5.45 \times 10^2$ mmol) in anhydrous DMSO and pyridine were added to N-hydroxysuccinimide activated chlorin $e_6$ (compound III) (37.7 mg, $5.45 \times 10^{-2}$ mmol) in the dark under a nitrogen atmosphere. After stirring at ambient temperature for 24 hrs, the mixture was gradually poured into a vigorously stirred solution of $Et_2O$ cooled to 0° C. The dark red precipitate obtained was collected by filtration, washed with $Et_2O$ and $CH_2Cl_2$ and dried under vacuum to prepare a final product. Compound II and Compound III were used as starting materials to yield 34 mg of the final product, Compound IV (yield: 55.8%).

Figure 4:
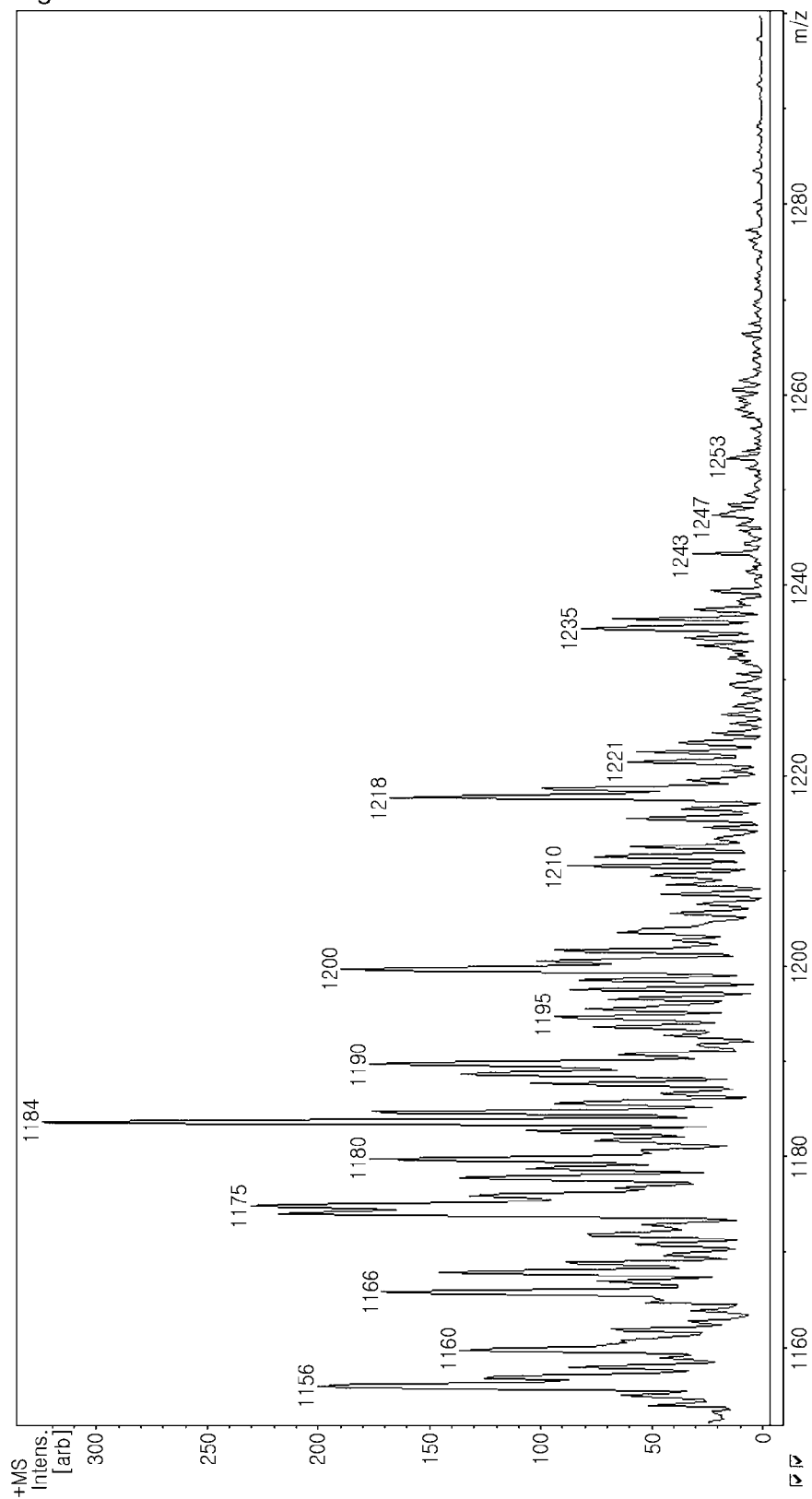
FIG. 4 is the result of mass spectrometry (Positive mode) of [γ-(6-aminohexyl)folic acid]-chlorin $e_6$.

The mass spectrometry (Positive mode) of the final product, Compound IV [(γ-(6-aminohexyl)folic acid]-chlorin $e_6$) showed that the molecular weight was 1183.46 (FIG. 4).

Figure 5:
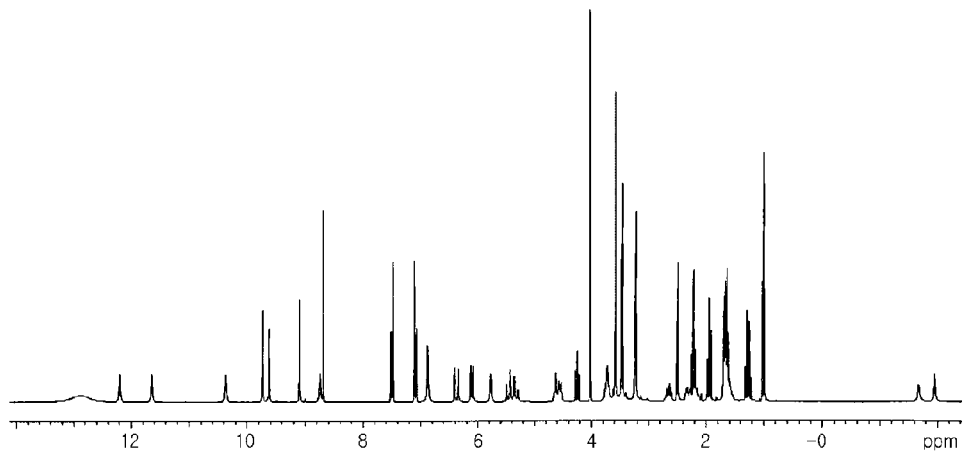
FIG. 5 is the result of NMR of [γ-(6-aminohexyl)folic acid]-chlorin $e_6$.

The NMR data of the final product, Compound IV [(γ-(6-aminohexyl)folic acid]-chlorin $e_6$) is shown in FIG. 5.

1H NMR (300 MHz, DMSO-d6): δ 12.2 (s, 1H, COOH), 11.68 (s, 1H, COOH), 10.37 (s, 1H, NH), 9.78 (s, 1H), 9.64 (s, 1H), 9.15 (s, 1H), 8.88 (s, 1H, NH), 8.8 (s, 1H), 8.20 (q, 1H), 7.56 (s, 2H), 7.15 (s, 2H), 6.89 (s, 2H, $NH_2$), 6.38 (d, 1H), 6.15 (d, 1H), 5.80 (s, 1H), 5.40 (m, 1H), 4.59 (m, 2H), 4.22 (t, 2H), 4.02 (s, 2H), 3.59 (s, 3H), 3.43 (s, 3H), 3.20 (s, 3H), 3.7 (q, 1H), 2.65 (m, 1H), 2.08-2.41 (m, 8H), 1.89 (t, 2H), 1.52-1.78 (m, 12H), 1.28 (m, 4H), 1.08-1.10 (m, 7H), −1.72 (s, 1H, NH), −1.96 (s, 1H, NH)

Experimental Example 1

Preliminary Studies on Preservation of Receptor Features in Folic Acid-Chlorin e6 Conjugate The synthesis of chlorin e6-folic acid conjugate prepared in Example 4 is based on the method of attachment of initial components (folic acid and chlorin e6) through carboxylic groups (—COOH).

To confirm whether folic acid in the content of obtained conjugate completely preserves its receptor features, electronic absorption spectrometry and fluorescence spectrometry were performed.

In the electronic absorption spectra, the specific maximum for chlorin appeared at 400 and 650 nm, and the specific maximum for folic acid appeared at 270 nm with the shoulder at 360 nm. In the fluorescence spectra of the conjugate, the maximum corresponding to chlorin appeared at 660 nm and 700 nm, and the specific maximum for folic acid appeared at 445 nm.

These results showed that folic acid in the content of obtained conjugate completely preserves its receptor features.

Comparative study of photosensitizing activities of free chlorin e6 and chlorin e6 in the conjugate demonstrated that chlorin e6 preserves the ability to generate singlet oxygen at excitation in the field of 600-700 nm and photosensitizing activity at joining conjugate even within the conjugate. The chlorine e6 within the conjugate expressed the same result as above both in a water solution and in an hydrophobic environment—in the case of binding of the conjugate with protein.

Experimental Example 2

Spectral-Energy Specifications of Chlorin e6 Conjugate and Generation Efficiency of Singlet Oxygen in Homogeneous and Heterogeneous Systems It was demonstrated that chlorin e6 could accumulate in tumor cells and tissues and stimulate their photosensitizing destruction. It is known that the abnormal functioning of cell membrane plays a prominent role in this process. This abnormal functioning is caused by oxidation of their protein and lipid components by a highly reactive oxidizing agent like singlet oxygen. The singlet oxygen is formed in the course of interaction between the molecules of environmental oxygen and molecules of photosensitizer in the activated triplet condition. Efficiency of $^1O_2$ generation is determined by a number of factors: absorbance capacity of sensitizer, power and quantum output of colonization of triplet conditions, duration of life in this condition, solubility and $O_2$ diffusion processes in environment, etc. It should be noted that the above mentioned factors could vary significantly while converting from homogeneous solutions of sensitizers to their complexes with biological systems being characterized by considerable heterogeneity. That is why spectral energy specifications of chlorin e6 conjugate and its efficiency of generation of singlet oxygen in various systems were examined in the present experimental example.

2-1 Experimental Method

Pigment-protein complexes have been formed by adding to the solution of human serum albumin (HAS) a specific amount of photosensitizer dissolved in the same buffer. The molar concentration ratio of HAS and chlorin e6 conjugate in this experiment was 2.5:1. Similarly, the photosensitizer was included in detergent micelle (Triton X-100, $C=10^{-3}M$). The complex of the chlorin e6 conjugate with egg lecithin-derived single-layer liposomes through gel filtration of lipid and pigment dispersion was formed.

The electronic absorption spectra of the subject solution were recorded on Specord UV-Vis. The fluorescence spectra and value of degree of fluorescence polarization (P) were recorded on an automatic spectrofluorimeter (Institute of Physics). Life time of photosensitizer fluorescence ($t_s$) was estimated using an impulse fluorometer operating in the mode of photons counting.

Based on new Hamamatsu FEU with InP/InGaAsP semiconductor photocathodes, a highly sensitive laser fluorometer for registration of luminescence signals in the range of 950-1400 nm with nanosecond time resolution was used.

2-2 Spectral Parameters

Figure 6:
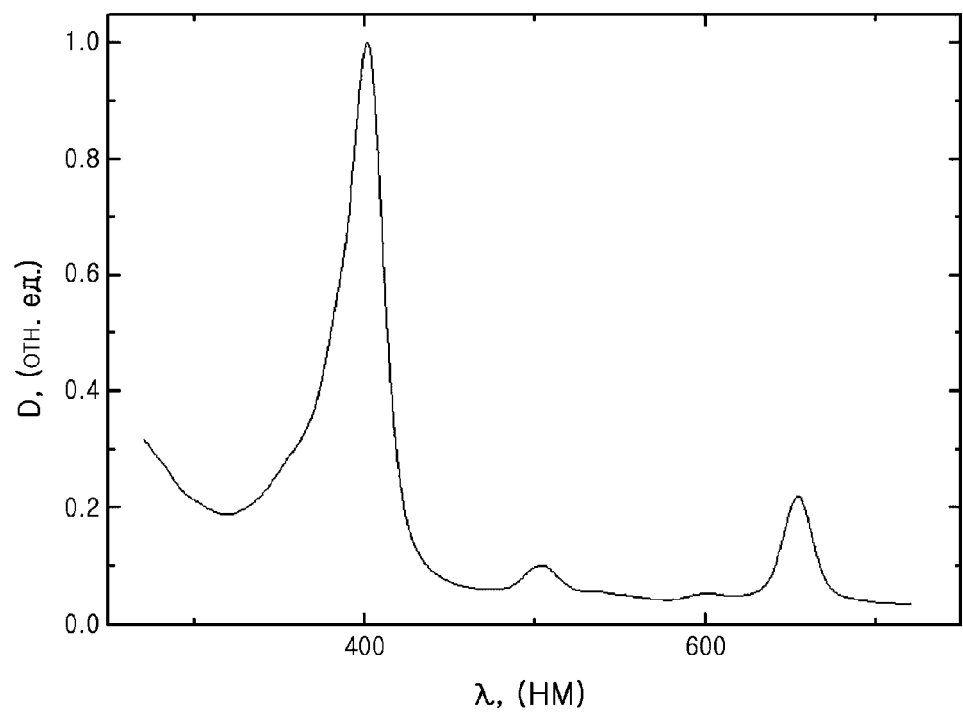
FIG. 6 shows the electronic absorption spectrum of chlorin e6 conjugate.

In a weakly alkali buffer (pH 7.4-8.1) at room temperature, the electronic absorption spectrum of chlorin e6 conjugate has a structure specific for porphyrin free base with hydrogenated C=C double bond (FIG. 6). The main feature of the absorption spectrum is intensive ($\epsilon=4.8 \cdot 10^4$ $M^{-1}$ $cm^{-1}$) $Q_x$ (0-0) band at 660 nm, which falls into the spectral window of the majority of biological tissues.

Figure 7:
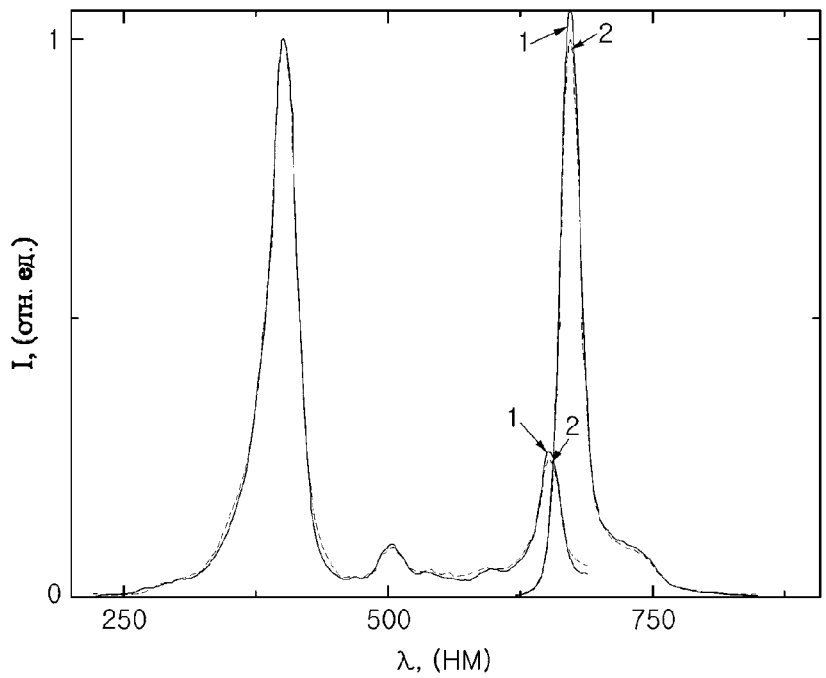
FIG. 7 shows the fluorescence spectrum and fluorescence excitation spectrum of chlorin e6 and chlorin e6 conjugate.

FIG. 7 shows the fluorescence spectra and fluorescence excited spectra of chlorin e6 and chlorin e6 conjugate in a buffer. The fluorescence spectra of both pigments do not depend on excitation wavelength, and the fluorescence excitation spectra of the pigments almost coincide with the absorption spectrum of chlorin e6. It should be noted that the excitation spectra of chlorin e6 conjugate differs from the absorption spectrum only in the "blue area" of the spectrum at 400-500 nm. In the excitation spectrum of the conjugate, there are no bands of absorption corresponding to absorption of the vectorial part (folic acid).

Complex formation of chlorin e6 conjugate, and HSA, liposomes or detergent micelles leads to bathochromic shift in the absorption and fluorescence spectra of pigment. However, an increase in fluorescence photoresponse (B) was observed, which correlates with the growth of life time ($t_s$) without changing of the Kravec integral value.

Similar changes of chlorin e6 conjugate spectral parameters are also observed in organic solvents decreasing polarity of medium.

Analysis of the obtained results leads to a conclusion that chlorin e6 conjugate in all the system is in a monomeric state, and spectral changes are caused mostly by orientational effects. In the present experiment, specific and orientational interactions play a minor role. The chlorin e6 conjugate in all the complexes has an hydrophobic surrounding, of which the polarity is equal to pyridine.

2-3 Photophysical Parameters

The quantum efficiency of the intercombinative conversion of chlorin e6 conjugate was determined by a relative method, according to which at minor ($\leq 10\%$) depletion of ground state the following Equation makes sense:

$$\gamma_{[k} = \gamma_0 \frac{\Delta D_{x,n} \Delta \epsilon_{\flat}^T \beta_{\flat}}{\Delta D_{\flat} \Delta \epsilon_{x,n}^T \beta_{x,n}}$$ [Equation 1]

wherein $\gamma_{[k}$ and $\gamma_{\flat}$ are respectively photoresponse of chlorin e6 conjugate intercombinative conversion and a standard material, $\Delta D_{x,n}$ and $\Delta D_{\flat}$ are respectively maximal deviations of triplet-triplet absorption of the studied and standard solutions on the wavelength of survey, $\Delta \epsilon_{x,n}^T$ and $\Delta \epsilon_{\flat}^T$ are respectively difference in molar ratio of extinction of singlet and triplet-triplet absorption of the chlorin and the standard material, and $\beta_{x,n}$ and $\beta_{\flat}$ are respectively shares of absorbed light by the chlorin and the standard material.

Values of $\Delta \epsilon_{x,n}^T$ and $\Delta \epsilon_{\flat}^T$ were determined after substantially transferring of all molecules of the studied substance in excited triplet state. In such conditions, $\Delta D=C\Delta \epsilon_T l$, wherein C indicates the molar concentration of the substance in solution, and l indicates the length of the optical way. As the standard to estimate $\gamma$, Pd(II)-octa ethyl porphyrin (Pd (II)-OEP) was selected, for which the $\gamma$ value in benzol was considered as equal to one. When measuring parameters of $\Delta \epsilon_T$, absorbances of solutions on excitation wavelength did not exceed 0.2 when $\gamma$ is 0.5, and corresponding concentrations of chlorin e6 conjugate did not exceed $0.7 \times 10^{-6}$ and $1.75 \times 10^{-5}$ M.

The obtained values of $\Delta \epsilon_T$ and $\gamma$ are shown in the following Table 2.

TABLE 1

Chlorin E6-conjugate fluorescent parameters in different systems

| System | $l^{00}_{abs}$ Nm | $l^{00}_{fl}$ nm | $t_S$ ns | B |
|---|---|---|---|---|
| H₂O, pH 8.1 | 657 | 664 | 4.3 | 0.16 |
| Triton X-100, pH 8.1 | 665 | 670 | 5.7 | 0.19 |
| HSA, pH 8.1 | 664 | 669 | 5.2 | 0.18 |
| Liposomes, pH 8.1 | 665 | 670 | 5.4 | 0.21 |
| Dimethyl sulfoxide | 661 | 672 | 4.6 | — |
| Pyridine | 666 | 673 | 5.0 | 0.18 |
| Tetrahydrofuran | 667 | 573 | 5.0 | — |
| Methanol | 662 | 667 | 4.8 | — |

TABLE 2

Photophysical parameters of chlorin e6 conjugate and the efficiency of $^1O_2$ generation in different systems

| System | $\tau_t^0$ µs | $\tau_t$ µs | $\Delta \epsilon^T$ mol⁻¹dm⁻¹cm⁻¹ | $\gamma$ | $\phi_\Delta$ |
|---|---|---|---|---|---|
| H₂O, pH 8.1 | 170 | 2.5 | 278 | 0.8 | 0.70 |
| Triton X-100 | 230 | 2.6 | | | 0.80 |
| HSA, H₂O, pH 8.1 | 700 | 14.7 | 798 | 0.82 | 0.63- |
| Liposomes, H₂O, pH 8.1 | 70 | 1.4 | 251 | 078 | — |
| Pyridine | 140 | 0.3 | 94 | 0.81 | 0.68 |

The photophysical parameters of chlorin e6 conjugate described in Table 2 are specific for the monomer state of pigment. As far as for all systems B+$\gamma \approx 1$, one could contend that the main way of electronic excitation energy degradation in the molecule of chlorin e6 conjugate, regardless of it's surrounding, is intercombinative conversion. Photoresponse of this process is high (γ≈0.7) and it is practically similar in all the systems. However, the lifetimes of excited triplet states in deoxygenated ($\tau_t^0$) and in oxygen saturated solutions (id are significantly different.

With respect to the liposomal forms of pigments, $\tau_t^0$ is almost 2.5 times lower than that of the buffer solution. High P value for chlorin e6 conjugate in liposomes (P=0.13) is evidence that pigments are in a rather tough circle in the lipid bilayer. Considering this circumstance, and also taking into consideration the photophysical characteristics of chlorin e6 conjugate in complex with liposomes, it is suggested that the decay of $\tau_t^0$ is caused probably by quenching of triplet states of pigment by carbon-carbon double bonds of non-saturated fatty-acid lipids chain.

2-4 Quenching of Excited Triplet States of Chlorin e6-Conjugate by Molecular Oxygen The data presented in Table 2 supports the analysis of specific features of quenching of excited triplet states of chlorin e6-conjugate by molecular oxygen in solutions and biological systems. Taking into consideration the obtained values of $\tau_t^0$ and $\tau_t$; $O_2$ concentrations in an aqueous solution ($2.6 \times 10^{-4}$ M), $O_2$ concentration in pyridine ($8.3 \times 10^{-4}$ M), and also considering that the distribution ratio between water and membrane phase is equal to 3, the bi-molecular rate constant for $O_2$ quenching of the triplet excited state of chlorin e6 conjugate can be estimated using the following equation 2:

$$\kappa_{\text{B}} = \left(\frac{1}{\tau_t} - \frac{1}{\tau_t^0}\right) / [O_2] \qquad \text{[Equation 2]}$$

It turned out that in these systems $\kappa_{\text{B}}$ values were equal correspondingly to $1.5 \times 10^9$, $4.5 \times 10^9$, and $9 \times 10^9$ $M^{-1}$ $c^{-1}$ for chlorin e6-conjugate in buffer solution, pyridine, and lipid bilayer, respectively. In pigment-protein and micellar complexes, the corresponding constant values of chlorin e6-conjugate were $2.5 \times 10^9$ and $1.5 \times 10^9$ $M^{-1}$ $c^{-1}$, respectively. These values are true if the $O_2$ concentration in the protein matrix and Trixon X-100 micelle does not differ from that in water solutions. Apparently, it is an upper limit of $\kappa_{\text{B}}$ values as far as it is known that the $O_2$ solubility in non-polar media is several times higher than its solubility in $H_2O$. Specific features of quenching of excited triplet states of chlorin e6-conjugate by molecular oxygen in pigment-protein complexes were examined. It is known that fluorescence of protein tryptophaniles is efficiently quenched by $O_2$, and corresponding bimolecular rate constants of quenching are in the range of $2 \times 10^9$ $M^{-1}$ $c^{-1}$~$5 \times 10^9$ $M^{-1}$ $c^{-1}$. Meanwhile, data of x-ray-structural analysis of globular proteins denote compact packing of amino acid residues, which causes significant steric obstacles for diffusion of molecules like $O_2$.

2-5 Generation of Singlet Oxygen

Photoresponse of this process ($\phi_A$) was measured by a relative method through integral intensity of singlet oxygen luminescence at a wavelength of 1270 nm. Excitation was conducted at a wavelength of 531 nm (pulse energy 4 microJ, frequency 1 kHz). Tests were made in air saturated buffer solutions at room temperature. Tetra(n-sulfophenyl) porphyrin (TSPP) was taken as a standard for $\phi_A$ measurement of chlorin e6-conjugate. The $\phi_A$ in $D_2O$ was considered as 0.7. Absorbances of solutions on excitation wavelength in all the cases did not exceed 0.1 (coating thickness: 10 mm).

Figure 8:
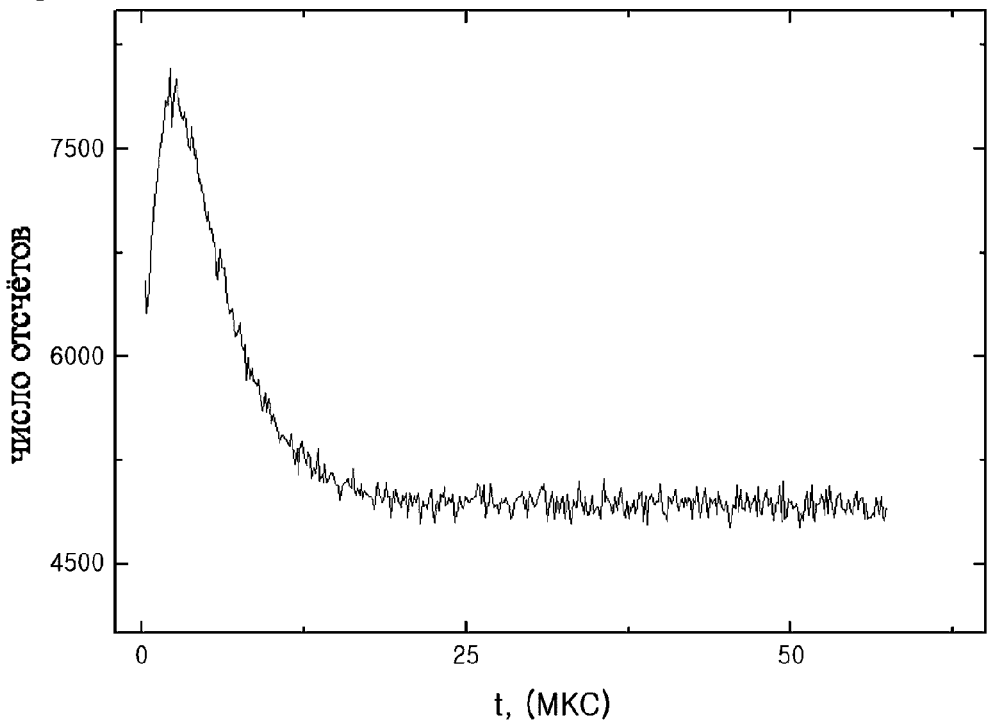
FIG. 8 is the result of luminescence kinetics of singlet oxygen photosensitized by the chlorin e6 conjugate.

The kinetics of luminescence of singlet oxygen photosensitized by chlorin e6-conjugate is shown in FIG. 8.

To analyze kinetic curves of singlet oxygen luminescence, the following function was used:

$$I(t) = \frac{A}{k_1 - k_2}[\exp(-k_2 t) - \exp(-k_1 t)]$$

wherein A is a coefficient depending on initial concentrations of interacted reagents, and $k_1$ and $k_2$ are constants of luminescence signal increase and extinction, respectively.

In the case when the deactivation rate constant $K_\tau$ of the photosensitizer triplet state exceeds the deactivation rate constant $K_A$ of the molecular oxygen triplet state, the constant of increase $k_1$ corresponds to $K_\tau$, and constant of extinction $k_2$ corresponds to $K_A$. In the case of $K_\tau < K_A$, inversion of the kinetics of singlet oxygen luminescence occurs. In this case, $k_2 = K_\tau$ and $k_1 = K_A$. In air saturated solutions in the absence of extinguishers, the first case was realized. Thus, based on kinetic data, the life times of singlet oxygen and triplet state can be calculated.

Therefore, on the basis of kinetic curves, the following values of $\tau_t$ and $\tau_A$ were obtained for chlorin e6-conjugate: 2.0±0.2 microsec. and 3.6±0.2 microsec., respectively. The mentioned values of life time of chlorin e6 conjugate in the triplet state correlated with $\tau_t$ obtained through the method of flesh-photolysis, and $\tau_A$ known in the literature. The photoresponse of the photosensitizing form of singlet oxygen of chlorin e6-conjugate decreased, as the pH of the solution decreased from 0.7 (pH 8.1) to 0.52 (pH 6.0), which was related to the generation of chlorin e6-conjugate aggregates by lowering the pH.

As shown in Table 2, molecules of a chlorin conjugate in a pyridine and buffer solution generate $^1O$ highly efficiently. The availability of protein in the solution leads to $\tau_A$ decrease approximately of 1.1, which corresponds to the bimolecular quenching constant, $\kappa_{\text{B}} = 1.5 \times 10^8$ $M^{-1}$ $c^{-1}$ Having known the concentrations of pigment ($3.1 \times 10^{-6}$ M) and protein ($C_o = 9.3 \times 10^{-6}$M) in the solution, as well as the constant value ($\kappa_{CB} = 1.2 \times 10^6 M^{-1}$), and the number of position binding with chlorin e6-conjugate (n=1), the share of sensibilizer molecules involved in pigment-protein complex can be estimated using the following Equation 3:

$$K_{CB} = r/C(C_\Sigma n - r) \qquad \text{[Equation 3]}$$

wherein r and C are the respectively concentrations of bound and unbound protein pigment, $r + C = C_\Sigma$. In this experiment, it is equal to 90%, which is why corresponding F values could be considered as generation efficiency of molecules of chlorin e6-conjugate built in protein globules. It is also applicable with respect to pigment molecules included in Triton X-100 micelle. Unfortunately, because of some methodical problems generated in the complex formation of chlorin e6-conjugate and single layer membranes, it failed to estimate F value. However, taking into consideration the photophysical parameters of chlorin e6 conjugate in a lipid bilayer, it can be suggested that $^1O_2$ generation efficiency should be at least not lower than in other studied complexes.

Taking into consideration the obtained results, it was confirmed that the chlorin e6 conjugate has optimal characteristics for effective generation of singlet oxygen in different media. Considering its unique tropism to tumor cells and tissues, it can be seen that the chlorin e6 conjugate of the present invention has much higher photodynamic activity than all currently known porphyrin-based photosensitizers.

Experimental Example 3

In Vitro Biological Effects of Chlorin e6 Conjugate of the Present Invention 3.1 Accumulation and Competition Assay The cellular accumulation and the targeted delivery of the photoactive compounds were investigated using Hela cells, which is one of the numerous tumor cell types that overexpress folate receptors.

Cells were cultivated for 3 days in medium 199, and transferred to Hank's solution/medium 199 (9/1). After 3 hours, the cell were collected by trypsin treatment from the substrate and placed in Hank's solution ($10^5$ к л /ml). To cell suspensions, chlorin e6 conjugates were added at a concentration of $2\times10^{-5}$ M/l, and incubated at 37° C. After 1, 5, 10, 15, and 24 hours, the samples were centrifuged, the pellet was washed with the cooled Hank's solution, and transferred to Hank's solution at a concentration being equal to that in the initial suspension. Relative concentrations of chlorin e6 and chlorin e6 conjugate in the obtained samples were measured by intensity of suspension fluorescence at $\lambda_{BO36}=405$ nm, $\lambda_{per}=665$ HM.

Table 3 shows the concentrations of chlorin e6 and chlorin e6 conjugate in Hela cells (relative units/$10^4$ cl.).

TABLE 3

| Incubation time (hours) | chlorin e6 | chlorin e6 conjugate |
|---|---|---|
| 1 | 0.86 | 0.40 |
| 5 | 1.45 | 1.80 |
| 10 | 1.72 | 2.50 |
| 15 | 0.81 | 12.5 |
| 24 | 0.40 | 15.0 |

As shown in Table 3, both free chlorin e6 and folic acid-chlorin e6 conjugate were accumulated in cells. However, the kinetic of accumulation is different. The majority of free chlorin e6 binds with cells within 5 hours, whereas binding of chlorin e6 conjugate increases linearly over 20 hours.

Figure 9:
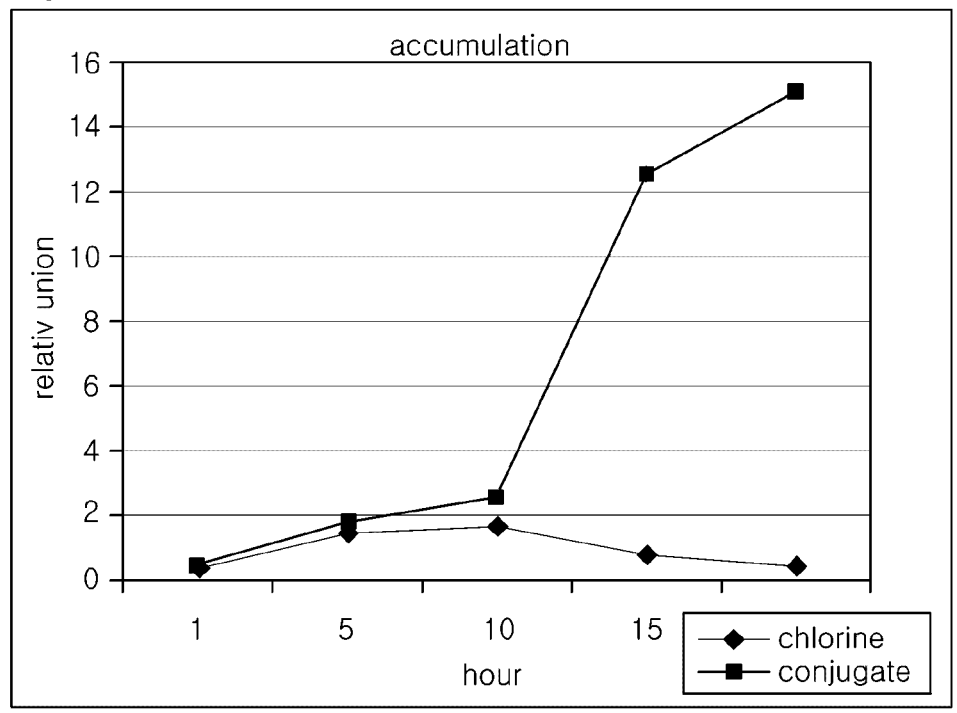
FIG. 9 is uptake kinetics of free chlorine e6 and chlorin e6 conjugate in Hela cells according to time.

After a 6 hr incubation, the accumulation of chlorin e6 conjugate is distinctly higher than the cellular uptake of free chlorin e6 (FIG. 9).

The cellular uptake of chlorin e6 conjugate after a 24 hr exposure was on average about 8-10-fold higher than that of free chlorin e6. The cellular uptake of chlorin e6 conjugate increased steadily over a 24 hr period, suggesting active transport via receptor-mediated endocytosis rather than nonspecific cell absorption.

In order to examine the effect of exogenous folic acid on free chlorin e6 and chlorin e6 conjugate uptake of hela cells, folic acid was added in a cellular suspension prior to chlorin introduction at a concentration of 4 µM/l, and incubated with free chlorin e6 and chlorin e6 conjugate for 24 hours. Then, the sample was centrifuged, the supernatant was taken, and the pellet was rewashed with cooled Hank's solution. The obtained pellet was again transferred into Hank's solution.

Fluorescence intensity was measured to compare their accumulation in Hela cells between chlorin e6 and chlorin e6 conjugate.

Figure 10:
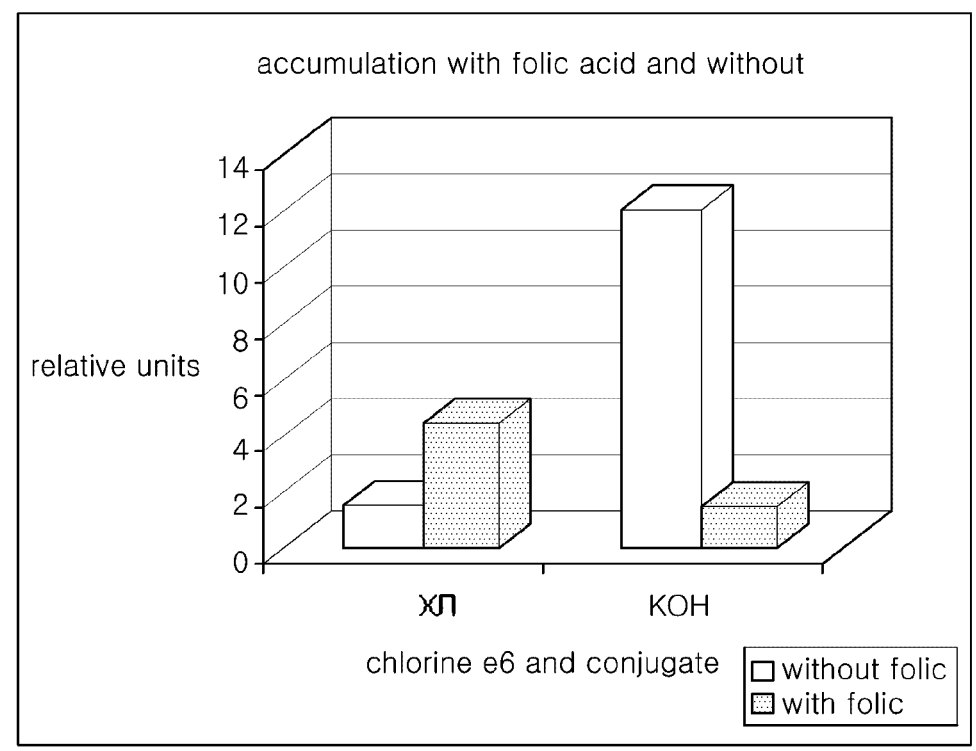
FIG. 10 is uptake kinetics of free chlorine e6 and chlorin e6 conjugate in Hela cells according to time after the addition of exogenous folic acid.

After a 24 hr exposure, the accumulation of chlorin e6 conjugate was higher than the cellular uptake of free chlorin e6. FIG. 10 shows that 4 µM/l of free folic acid significantly reduced the uptake of chlorin e6 conjugate in Hela cells ($p<0.05$), but had no significant effect on chlorin e6 uptake. Actually, the cellular uptake of chlorin e6 was not influenced by the presence of a competitive concentration of folic acid in the culture medium. However, despite the decrease of conjugate accumulation in the presence of competing folic acid, cellular accumulation remained superior to free chlorin e6, suggesting that the presence of folic acid could also increase nonspecific uptake.

3.2 Cytotoxicity (Antiproliferative Assay)

Cytotoxicity was analyzed, considering the intensity of proliferative processes in cells, photosensitizer concentration, and dose of optical power. For each point, 3 flasks with cell monolayer were used.

The monolayer culture of HeLa tumor cells was chosen and used as the cell.

The culture of HeLa tumor cells was grown in nutrient medium 199 or in nutrient medium containing hemohydrolyzate supplemented with 10% fetal bovine serum and 100 mg/ml of kanamycin.

On day 4 after the cell culture was inoculated in the flasks (100,000 cells per 2.0 ml of nutrient medium), the photosensitizer was added at a concentration of 1, 2.5, 5.0, 10.0, 20.0, or 30.0 mg/ml.

Flasks with light-protective cover (dark cytotoxicity) were incubated at 37.5° C. for 1 hour. The cells were washed with Hank's solution 4 times. 2.0 ml of fresh nutrient medium were added, and the cells were irradiated at the temperature of melting ice for 5, 10, 15 or 20 mins by the light flux of a "METALAZ" laser medical device (wavelength: 627.8 nm, 578.2 or 510.6 nm) or "LD 680-2000" (wavelength: 670-690 nm), depending on the wavelength of maximum spectral absorption of the studied photosensitizer, at a dose of 40 J/cm$^2$. After 20-24 hours, the number of tumor cell was counted in Goriaev's chamber.

Table 4 shows the number of HeLa cells (in percentage of the control) after incubation for 24 hours.

TABLE 4

| Photosensitizer Conc. (µm) | Chlorin e6 | Chlorin e6 conjugate |
|---|---|---|
| 1 | 101.3 | 102.1 |
| 2.5 | 99.1 | 95.6 |
| 5.0 | 98.4 | 94.1 |
| 10.0 | 95.5 | 95.9 |
| 20.0 | 90.0 | 89.0 |
| 30.0 | 89.7 | 86.6 |

Figure 11:
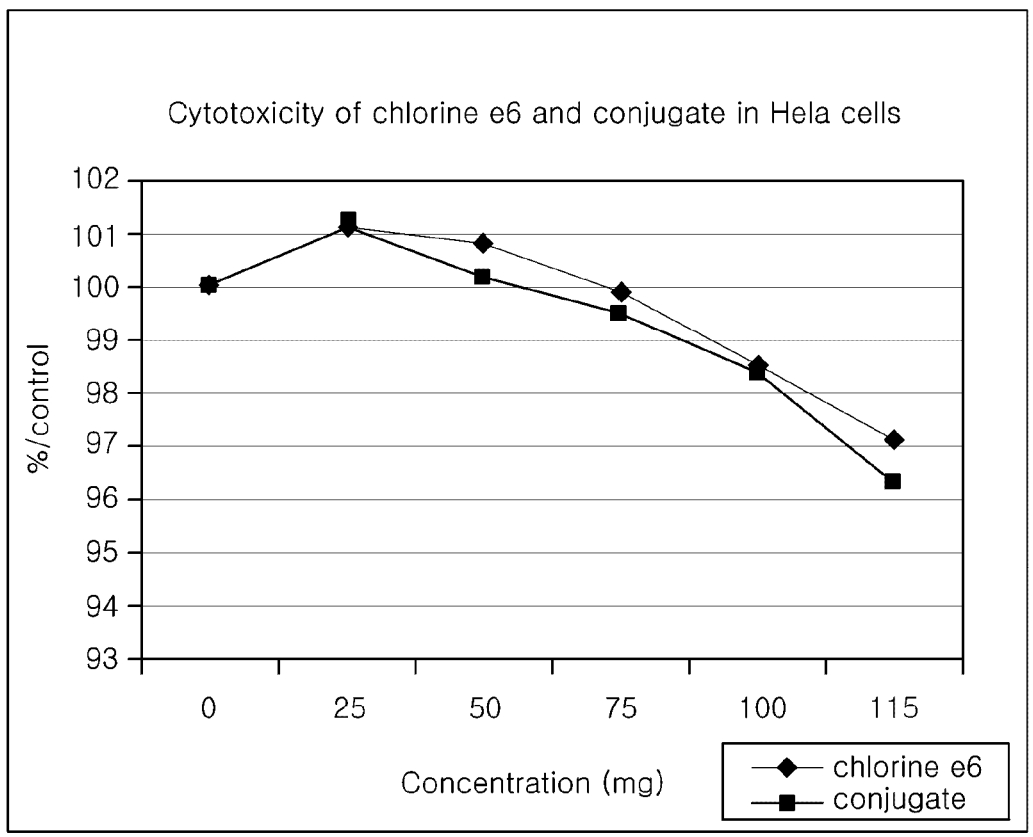
FIG. 11 shows the concentration-dependent cytotoxicity of free chlorin e6 and chlorin e6 conjugate in Hela cells in the absence of light exposure.

As shown in Table 4, the cell survival rates were about 90%, which demonstrated that 24 hr incubation of Hela cells with photoactive compound (chlorin e6 and chlorin e6 conjugate) induced no cytotoxicity in the absence of light exposure (FIG. 11). The addition of folic acid also did not affect the above results.

3.3 Phototoxicity (Photodynamic Activity) of Chlorin e6 Versus Chlorin e6 Conjugate To examine the photodynamic effects of a photosensitizer on a HeLa cell culture, the photosensitizer solution was added to the nutrient media at a final concentration of 0.1, 0.5, 1.0, 5.0 or 10 mcg/ml on day 3 after transplanting the cell culture into flasks. The flasks were wrapped with a light protecting cover, and incubated at 37° C. for 3.5 hours. Then, the cells were washed with Hank's solution, and exposed on ice by a laser medical device "LD 680-2000" (wavelength: 670-690 nm) at a dose of 3.3 joule/cm$^2$. After 20-24 hours, the available cell monolayer was dispersed using a 0.02%-Versene solution, and the number of tumor cells was calculated in Goriaev's chamber. For each point, 3 flasks were used.

Table 5 shows the number of HELA cells (relative to the control) after incubation with the photosensitizer for 3.5 hours and further photoexposure (PhE) at a dose of 3.3 joule/cm$^2$.

TABLE 5

| Photosensitizer Conc. (mcg/ml) | Chlorin e6 | Chlorin e6 conjugate |
|---|---|---|
| 0.1 | 87.1 | 65.1 |
| 0.5 | 83.6 | 42.3 |
| 1.0 | 64.7 | 12.6 |
| 5.0 | 19 | 0.1 |
| 10.0 | 3.8 | — |

Figure 12:
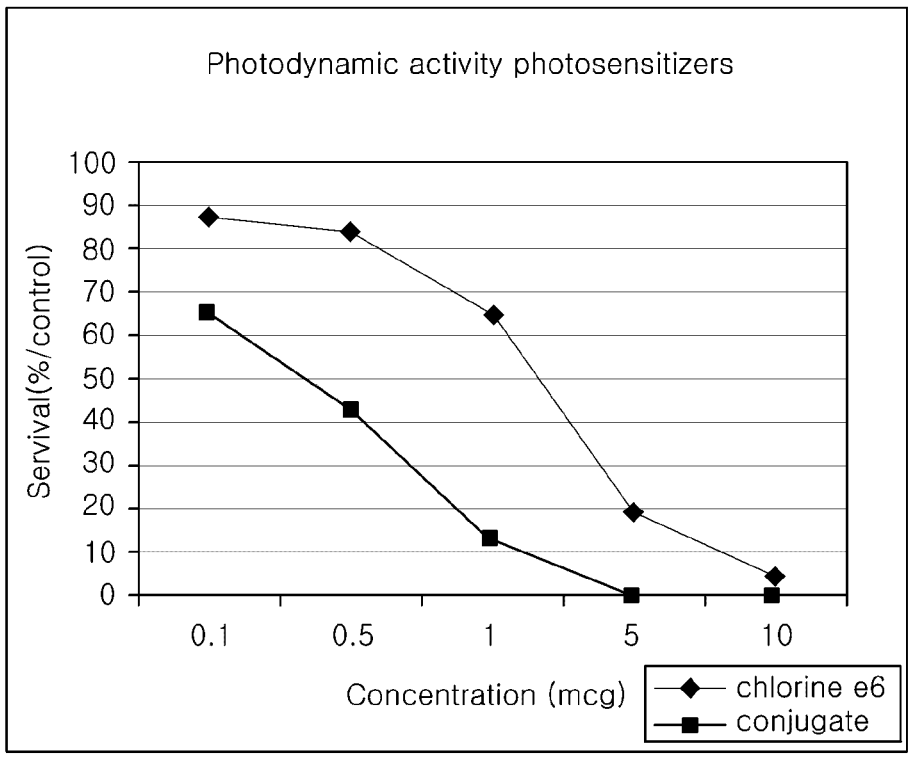
FIG. 12 shows the concentration-dependent photodynamic activity of free chlorin e6 and chlorin e6 conjugate.

The study on photodynamic activity revealed its high efficiency. The chlorin e6 conjugate fully inhibited the proliferation of Hela cells at the concentration of 5-10 mcg/ml (FIG. 12).

In other experiment, the cells were incubated with photosensitizers at 37° C. for 24 hours, and irradiated by exposed on ice by a laser medical device "LD 680-2000" (wavelength of 670-690 nm) in a dose of 1.5-15 joule/cm$^2$.

Figure 13:
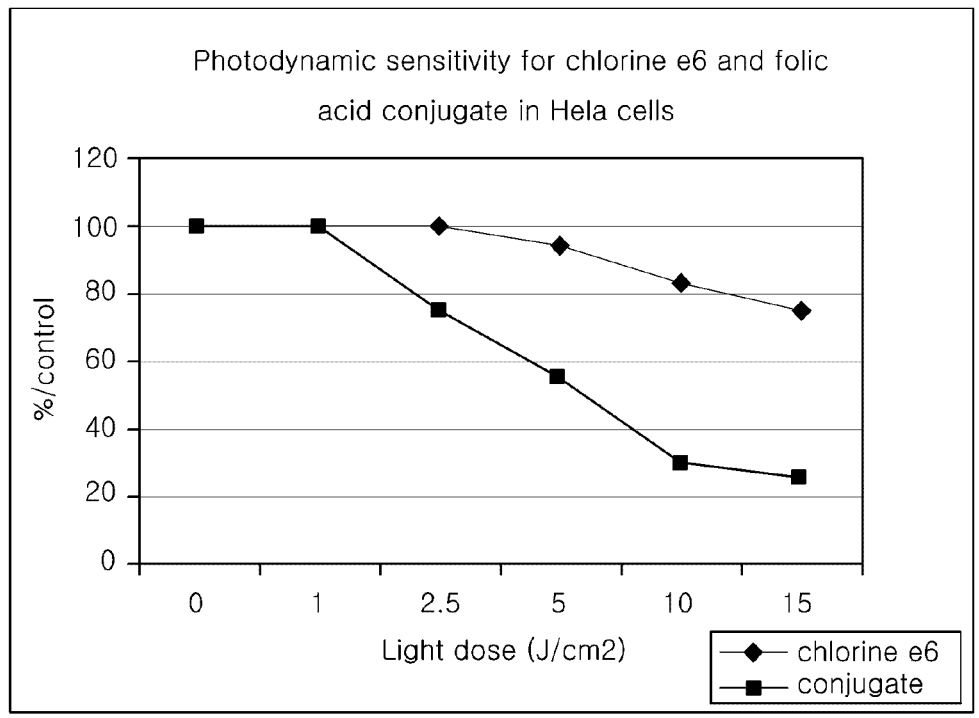
FIG. 13 shows the photodynamic activity of free chlorin e6 and chlorin e6 conjugate in Hela cells, after light exposure of 3.3 J/cm$^2$.

FIG. 13 shows that the control photosensitizer, chlorin e6 displayed little phototoxicity in this experimental conditions. On the contrary, it was demonstrated that in the survival test, the chlorin e6 conjugate improved the photosensitivity compared to chlorin e6-mediated photosensitivity.

This experiment demonstrated that the photobiological activity of chlorin e6 was improved by conjugation with folic acid.

Thus, the chlorin e6 conjugate accumulated on average about 10-fold higher than chlorin e6, after 24 hr incubation using Hela cells that overexpress the folate receptor.

Tumor cells are known to exhibit considerable variation in the number and types of receptors that they overexpress, relative to healthy tissues. The overexpression of a given receptor is often applied for targeted delivery of a photosensitizer to tumor cells. In Hela cells in which the folate receptor is overexpressed, a folate-targeting ligand is used.

It is concluded that the cellular uptake of chlorin e6 conjugate in Hela cells is folate-specific and is much more potent than non-conjugated chlorin e6.

Experimental Example 4

In Vivo Biological Effects of Chlorin e6 Conjugate of the Present Invention 4-1 Accumulation Kinetics of Photosensitizer Upon Photoexposure of Rats with Sarcoma M-1

First, accumulation of the photosensitizer upon photoexposure of rats with sarcoma M-1 was examined.

The accumulation kinetics of two photosensitizers (chlorin e6 and chlorin e6 conjugate) was examined in tumor and normal tissue of rats with sarcoma M-1 after intravenous administration of the photosensitizers at a dose of 2.5, 5.0 and 10.0 mg/kg.

The experiments were conducted on 100 white outbred rats with subcutaneous transplantation of sarcoma M-1, 7-9 days after tumor transplant. Photosensitizers were introduced to the animals via an intravenous route, once at a dose of 2.5, 5.0 and 10.0 mg/kg in a room with a low level of light. A sterile isotonic solution of sodium chloride was used as a solvent. Follow up over the dynamics of photosensitizer accumulation in tumor and normal tissues was conducted at 30 mins, 1-5 hours, and 1-6 days after photosensitizer administration.

In tumor tissues of rats with sarcoma M-1 and normal tissues (skin of opposite haunch), the dynamics of photosensitizer accumulation was analyzed by the method of measurement of life time using computer fluorescent spectrophotometry. For this purpose, a laser-fiber spectroanalyzer "LESA-6" with a helium-neon diagnostic laser "LHN 633-25" (BIOSPEC, Moscow) was used. This allows an estimate locally of the level of photosensitizer accumulation in any organs and tissues accessible for an optical fiber probe.

For real time monitoring at every hour after administration of the drug, the distal end of a catheter was placed over the tumor and normal tissues, and the intensity of the drug accumulation was recorded on the wave length corresponding to maximum fluorescence.

The obtained digital values of considered indices were processed by commonly accepted statistical methods using the computer program Origin 6.1. The significance level was equal to 0.05.

Figure 14:
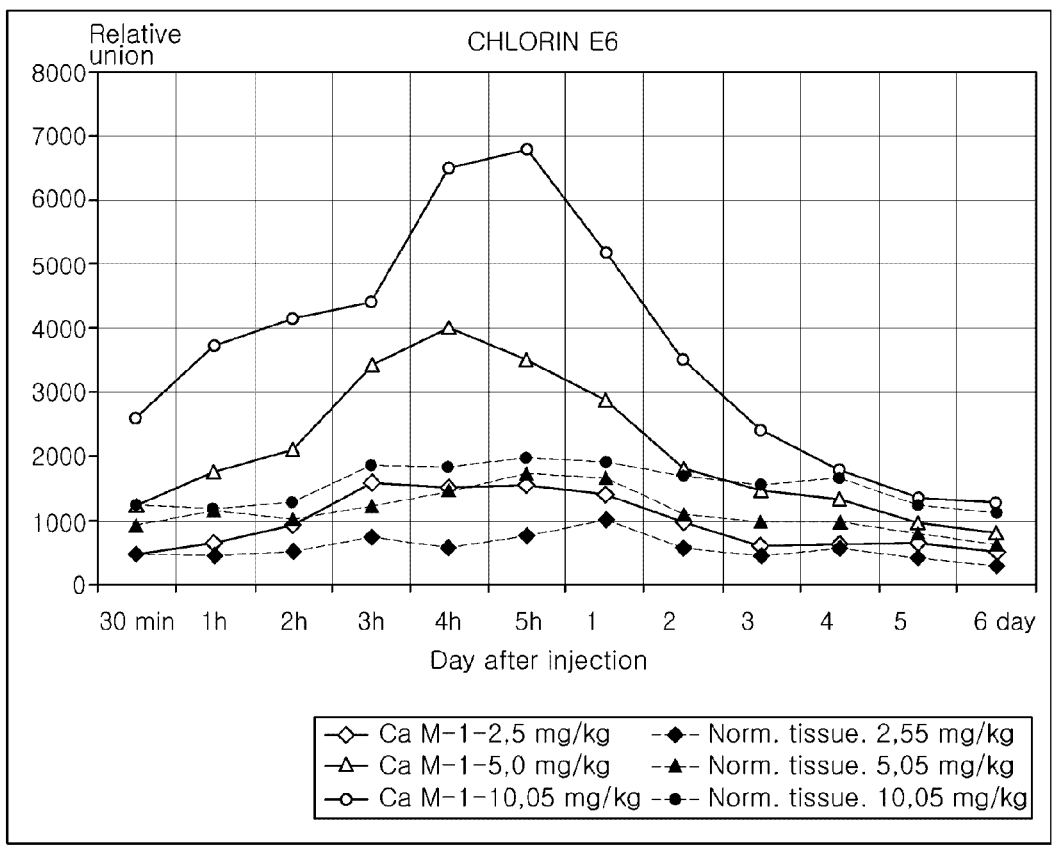
FIG. 14 shows the accumulation dynamics of chlorin e6 in sarcoma M-1 and normal tissues of rats after administration of chlorin e6 in a dose of 2.5, 5.0 and 10.0 mg/kg.
Figure 15:
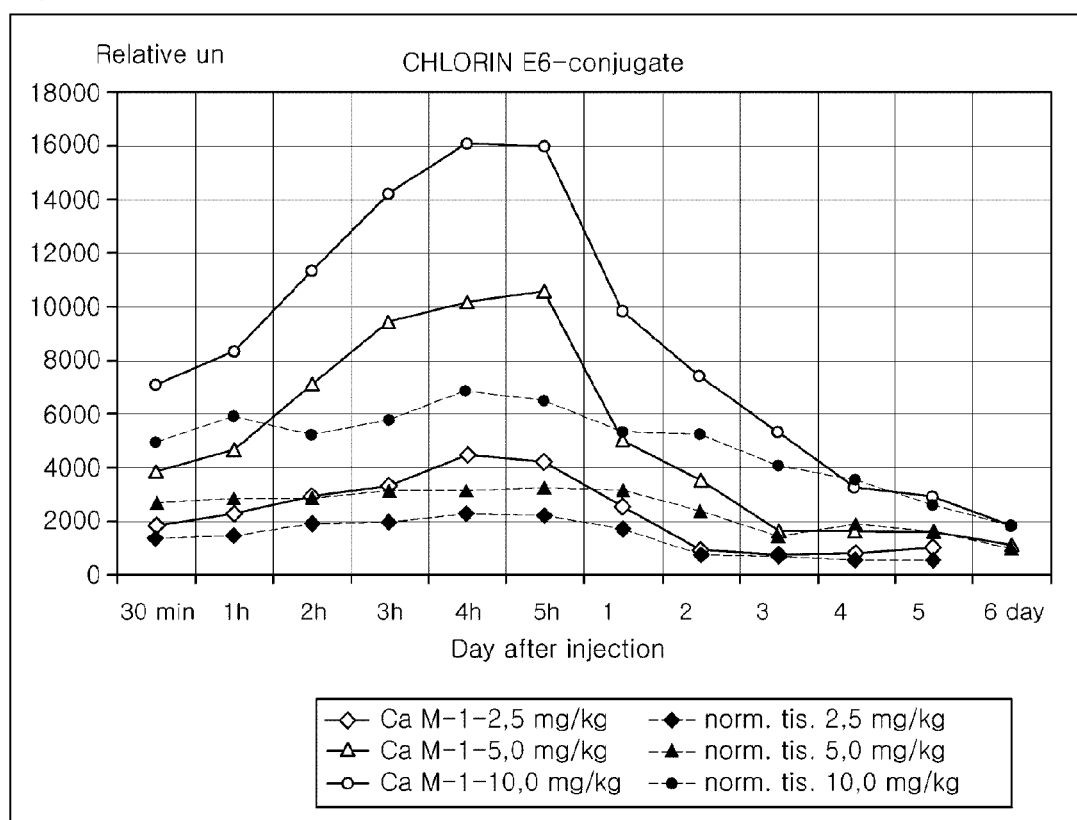
FIG. 15 shows the accumulation dynamics of chlorin e6 conjugate in sarcoma M-1 and normal tissues of rats after administration of chlorin e6 conjugate in a dose of 2.5, 5.0 and 10.0 mg/kg.

The data of fluorescence levels in sarcoma M-1 and normal tissues of rats during the first 5 hours and 1-6 days following the administration of chlorin e6 and chlorin e6 conjugate are shown in FIGS. 14 and 15. The accumulation of both photosensitizers was 2-3 times higher in tumor tissue than in normal tissue by 4-5 hours regardless doses.

Estimation of the selectivity ratio (aver. accumulation in tumor/aver. accumulation in normal tissue) showed that the maximum accumulation of chlorin e6 in tumor tissue of rats was recorded in the first 5 hours after its intravenous administration of 10.0 mg/kg. The maximum accumulation of chlorin e6 conjugate was recorded in the period of 2-5 hours after its administration of 5.0 mg/kg.

4-2 Antitumor Effects of Photosensitizer on Rats with Sarcoma M-1 Upon Photoexposure The necrotic area in rats with sarcoma M-1 was monitored after intravenous administration of chlorin e6 conjugate at a dose of 2.5, 5.0 or 10.0 mg/kg and photoexposure in a dose of 100 J/cm$^2$.

Anti-tumor efficiency of PDT with chlorin e6 conjugate was monitored for 24 hours after photoexposure in a dose of 100 J/cm$^2$ (laser instrument "LD680-2000") by quantitative assessment of necrotic areas formed in tumors at vital staining by 0.6% Evans blue (1 ml per 100 g of body weight). 2 hours later the animals were killed by chloroform, the tumor was excised and fixed for one hour in 10%-HOM formalin. After fixation, transverse sections of the tumor nodule in its highest diameter were made, and pictures were taken by a camera connected to a computer.

For quantitative assessment of necroses formed after PDT, computer analysis of color tints of histo-topographic tumor slides was performed using a special program.

The program included an algorithm of blue color identification (Evans blue), which stained viable areas of the tumor. Tumor areas killed from direct cytotoxic effect or due to structural-functional disorders of microcirculation were not stained in blue. The ratio of all non-stained dots to the total amount of dots in the fence of the tumor slide was considered to be the destruction efficiency.

Photoexposure of tumors was conducted at 1 hour and 4 hours after intravenous administration of the chlorin e6 conjugate, based on the obtained data of spectral-fluorescent monitoring of chlorin e6 conjugate accumulation in sarcoma M-1.

For this purpose, a laser medical instrument "ЛД 680-2000" (BIOSPEC, Moscow) was used to perform the exposure at a wavelength of 670 nm in a dose of 100 J/cm$^2$. The power density was 0.51 W/cm$^2$, the output power was 0.4 W, and the spot light diameter was 1 cm. Time of exposure was 3.27 sec. Monitoring over radiating power was conducted by a universal power meter included in the laser device "ЛД 4680-2000".

Tables 6 to 10 show the data of necrotic areas in 75 histo-topographic slides of rats with sarcoma M-1, in which the necrotic areas were formed after administration of a sample of chlorin e6 conjugate in a dose of 2.5, 5.0 or 10.0 mg/kg and PDT in a dose of 100 J/cm².

PDT with chlorin e6 conjugate in a dose of 2.5 mg/kg caused necrosis in 25.56±1.65%. After application of the photosensitizer in a dose of 5.0 mg/kg, the area of necrosis was increased to 34.16±2.16%. At 4 hr exposure after application of chlorin e6 conjugate in a dose of 10.0 mg/kg, 66.16±3.83% of tumor was destroyed. The most prominent anti-tumor effect was recorded at 1 hr exposure after application of chlorin e6 conjugate in a dose of 10.0 mg/kg.

TABLE 6

Necrotic area in histo-topographic slides of sarcoma M-1 in rats by PDT in dose of 100 J/cm² at 4 hours after application of chlorin e6 conjugate of 2.5 mg/kg

| Slide No. | Slide area of sarcoma M-1, cm² | Necrotic area, cm² | Ratio of necrotic area to total area, % |
|---|---|---|---|
| 1 | 2.409 | 0.568 | 24 |
| 2 | 2.209 | 0.378 | 17 |
| 3 | 2.457 | 0.460 | 19 |
| 4 | 2.735 | 0.409 | 15 |
| 5 | 2.687 | 0.488 | 18 |
| 6 | 2.761 | 0.864 | 31 |
| 7 | 2.635 | 0.832 | 32 |
| 8 | 2.611 | 0.858 | 33 |
| 9 | 2.394 | 1.038 | 43 |
| 10 | 2.519 | 0.899 | 36 |
| 11 | 2.190 | 0.498 | 23 |
| 12 | 2.348 | 0.579 | 25 |
| 13 | 2.394 | 0.754 | 32 |
| 14 | 2.571 | 0.778 | 30 |
| 15 | 2.780 | 0.996 | 36 |
| 16 | 2.363 | 0.661 | 28 |
| 17 | 2.093 | 0.565 | 27 |
| 18 | 2.212 | 0.795 | 36 |
| 19 | 2.636 | 0.627 | 24 |
| 20 | 2.805 | 0.808 | 29 |
| 21 | 2.587 | 0.414 | 16 |
| 22 | 2.504 | 0.357 | 14 |
| 23 | 2.942 | 0.394 | 13 |
| 24 | 2.471 | 0.369 | 15 |
| 25 | 2.377 | 0.547 | 23 |
| X± | 2.508 | 0.637 | 25.56 |
| Sd | 0.042 | 0.041 | 1.651 |

TABLE 7

Necrotic area in histo-topographic slides of sarcoma M-1 in rats by PDT in dose of 100 J/cm² at 4 hours after application of chlorin e6 conjugate of 5.0 mg/kg

| Slide No. | Slide area of sarcoma M-1, cm² | Necrotic area, cm² | Ratio of necrotic area to total area, % |
|---|---|---|---|
| 1 | 2.149 | 0.433 | 20 |
| 2 | 2.412 | 0.668 | 28 |
| 3 | 2.640 | 0.691 | 26 |
| 4 | 1.886 | 0.521 | 28 |
| 5 | 2.664 | 0.792 | 30 |
| 6 | 2.450 | 0.732 | 30 |
| 7 | 2.913 | 0.837 | 29 |
| 8 | 2.845 | 0.994 | 35 |
| 9 | 2.409 | 0.931 | 39 |
| 10 | 2.510 | 0.998 | 40 |
| 11 | 1.937 | 0.474 | 24 |
| 12 | 1.374 | 0.602 | 44 |
| 13 | 1.598 | 0.901 | 56 |
| 14 | 1.412 | 0.642 | 46 |
| 15 | 1.663 | 0.947 | 57 |
| 16 | 1.814 | 0.978 | 54 |
| 17 | 2.226 | 0.548 | 25 |
| 18 | 1.813 | 0.531 | 29 |
| 19 | 2.292 | 0.489 | 21 |
| 20 | 3.105 | 0.927 | 30 |
| 21 | 2.227 | 0.647 | 29 |
| 22 | 3.117 | 0.841 | 27 |
| 23 | 2.835 | 0.810 | 29 |
| 24 | 2.172 | 0.662 | 30 |
| 25 | 1.924 | 0.932 | 48 |
| X± | 2,255 | 0.741 | 34.16 |
| Sd | 0.100 | 0.036 | 2.163 |

TABLE 8

Necrotic area in histo-topographic slides of sarcoma M-1 in rats by PDT in dose of 100 J/cm² at 4 hours after application of chlorin e6 conjugate of 10.0 mg/kg

| Slide No. | Slide area of sarcoma M-1, cm² | Necrotic area, cm² | Ratio of necrotic area to total area, % |
|---|---|---|---|
| 1 | 1.399 | 0.913 | 65 |
| 2 | 1.368 | 0.908 | 66 |
| 3 | 1.422 | 1.026 | 72 |
| 4 | 1.533 | 1.196 | 78 |
| 5 | 1.734 | 1.606 | 93 |
| 6 | 1.672 | 1.539 | 92 |
| 7 | 1.724 | 1.473 | 85 |
| 8 | 1.574 | 1.423 | 90 |
| 9 | 2.207 | 0.720 | 33 |
| 10 | 2.503 | 0.860 | 32 |
| 11 | 1.961 | 1.009 | 51 |
| 12 | 2.105 | 1.231 | 58 |
| 13 | 1.891 | 1.690 | 89 |
| 14 | 2.007 | 1.803 | 90 |
| 15 | 1.719 | 1.346 | 78 |
| 16 | 1.460 | 0.988 | 68 |
| 17 | 2.613 | 0.762 | 29 |
| 18 | 1.655 | 1.313 | 79 |
| 19 | 2.124 | 1.075 | 51 |
| 20 | 2.414 | 1.279 | 53 |
| 21 | 2.034 | 1.405 | 69 |
| 22 | 2.357 | 1.165 | 49 |
| 23 | 2.451 | 1.297 | 53 |
| 24 | 1.668 | 1.199 | 72 |
| 25 | 1.557 | 0.919 | 59 |
| X± | 1.886 | 1.205 | 66.16 |
| Sd | 0.075 | 0.058 | 3.828 |

TABLE 9

Growth dynamics of sarcoma M-1 in rats after PDT with chlorin e6 conjugate, expressed as time-dependent $cm^3$ after tumor transplant

| | 7 | 10 | 12 | 14 | 17 | 19 | 21 | 24 |
|---|---|---|---|---|---|---|---|---|
| Control group | 0.46 ± 0.03 | 1.36 ± 0.09 | 2.75 ± 0.34 | 4.03 ± 0.43 | 8.87 ± 0.66 | 11.53 ± 0.6 | 16.61 ± 0.59 | 18.61 ± 0.78 |
| 2.5 mg/kg + 100 $J/cm^2$ for 1 h | 0.25 ± 0.03 | 0.28 ± 0.03 | 0.34 ± 0.06 | 0.41 ± 0.09 | 0.46 ± 0.11 | 0.69 ± 0.27 | 0.96 ± 0.38 | 1.19 ± 0.48 |
| 5 mg/kg + 100 $J/cm^2$ for 1 h | 0.29 ± 0.02 | 0.300 ± .03 | 0.30 ± 0.03 | 0.30 ± 0.03 | 0.37 ± 0.05 | 0.47 ± 0.11 | 0.50 ± 0.14 | 0.54 ± 0.17 |
| 10 mg/kg + 100 $J/cm^2$ for 1 h | 0.20 ± 0.03 | 0.19 ± 0.04 | 0.17 ± 0.03 | 0.17 ± 0.03 | 0.17 ± 0.03 | 0.17 ± 0.03 | 0.20 ± 0.03 | 0.20 ± 0.03 |

TABLE 10

Growth inhibition rate of sarcoma M-1 of rats to the control after PDT with chlorin e6 conjugate

| | Growth inhibition rate of sarcoma M-1 of rats in volume on days | | | | | | | |
|---|---|---|---|---|---|---|---|---|
| Dose | 7 | 10 | 12 | 14 | 17 | 19 | 21 | 24 |
| 2.5 mg/100 g + 100 $J/cm^2$ for 1 h | 47.5 | 79.4 | 87.6 | 89.8 | 94.8 | 94.1 | 94.2 | 93.6 |
| 5 mg/100 g + 100 $J/cm^2$ for 1 h | 36.9 | 77.9 | 89.1 | 92.6 | 95.8 | 95.9 | 96.9 | 97.1 |
| 10 mg/100 g + 100 $J/cm^2$ for 1 h | 56.5 | 86.0 | 93.8 | 95.8 | 98.1 | 95.2 | 98.8 | 98.9 |

The spectral-fluorescent studies of chlorin e6 and chlorin e6 conjugate accumulation were performed by life time laser fluorescent spectroscopy, resulting in that the maximum accumulation of chlorin e6 in tumor tissue of rats with sarcoma M-1 was recorded during the first 5 hours after its intravenous administration of 10.0 mg/kg. The maximum accumulation of chlorin e6 conjugate was recorded during 2 to 5 hours after its administration of 5.0 mg/kg.

When analyzing anti-tumor effect through calculation of the necrotic area formed in sarcoma M-1 after PDT with chlorin e6 conjugate of 2.5, 5.0 and 10 mg/kg, it was found that the most prominent effect was recorded at application of 10.0 mg/kg, and the necrosis ratio was 66.16%.

For 24 days after PDT with chlorin e6 conjugate, the growth inhibition effects on sarcoma M-1 of rats were monitored by volume comparing to the control, resulting in the inhibition rate of 86.34-99.1%.

A study for comparison of the cellular uptake indicates that the chlorin e6 conjugate possesses an enhanced affinity for tumor cells and cellular membranes. Comparison of the uptake in the induced sarcoma shows that the chlorin e6 conjugate is a much better tumor localizer than free chlorin e6. The efficiency of phototherapy with chlorin e6 conjugate is higher than that with free chlorin e6.

Taken together, it could be concluded that chlorin e6 conjugate has optimal characteristics for effective generation of singlet oxygen in different media. Considering its unique tropism to tumor cells and tissues, it can be seen that the chlorin e6 conjugate of the present invention has much higher photodynamic activity than all currently known porphyrin-based photosensitizers.

The invention claimed is:

1. A chlorin e6-folic acid conjugate represented by the following Formula 1 or 2, or a pharmaceutically acceptable salt thereof:

[Formula 1]

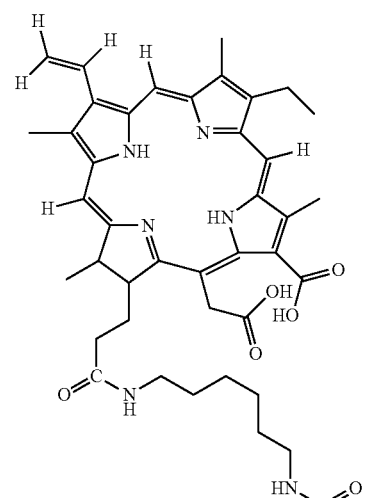

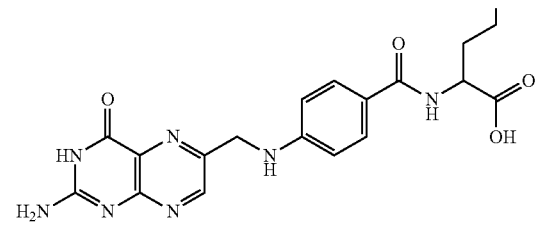

[Formula 2]

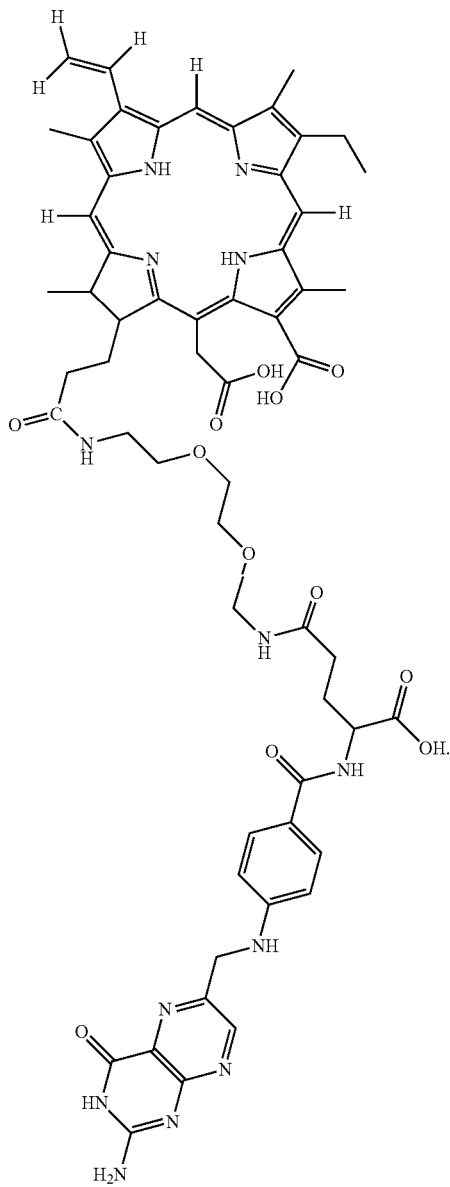

2. A method for preparing a chlorin e6-folic acid conjugate that is represented by the following Formula 1 or 2, or a pharmaceutically acceptable salt thereof, comprising the steps of:

reacting folic acid with [tert-butyl-N-(6-aminohexyl)]carbamate or tert-butyl 2-(2-(2-aminoethoxy)ethoxy)ethyl-carbamate under a nitrogen atmosphere at room temperature to obtain γ-{[tert-butyl-N-(6-aminohexyl)]carbamate}folic acid or γ-{N-{2-[2-(2-aminoethoxy)ethoxy]ethyl carbamate}folic acid;

treating γ-{[tert-butyl-N-(6-aminohexyl)]carbamate}folic acid or γ-{N-{2-[2-(2-aminoethoxy)ethoxy]ethyl carbamate}folic acid of the above step with trifluoroacetic acid to obtain γ-(6-aminohexyl)folic acid or γ-{N-{2-[2-(2-aminoethoxy)ethoxy]ethyl}}folic acid; adding N-hydroxysuccinimide and dicyclohexylcarbodiimide to chlorin e6 in the dark under a nitrogen atmosphere to obtain chlorin e6 succinidyl ester; and adding chlorin e6 succinidyl ester to the prepared γ-(6-aminohexyl)folic acid or γ-{N-{2-[2-(2-aminoethoxy)ethoxy]ethyl}}folic acid in the dark under a nitrogen atmosphere to prepare [γ-(6-aminohexyl)folic acid]-chlorin e6 or {γ-{N-{2-[2-(2-aminoethoxy)ethoxy]ethyl}folic acid}}-chlorin e6

[Formula 1]

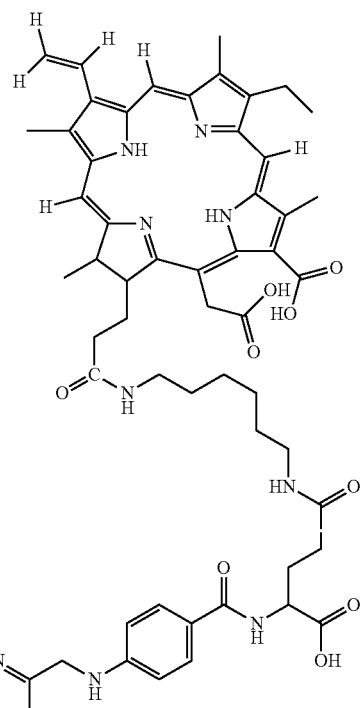

[Formula 2]

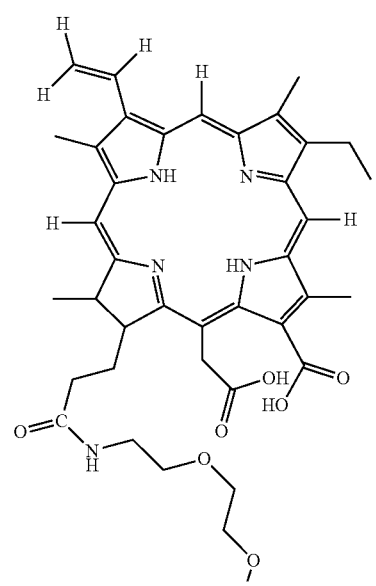

-continued
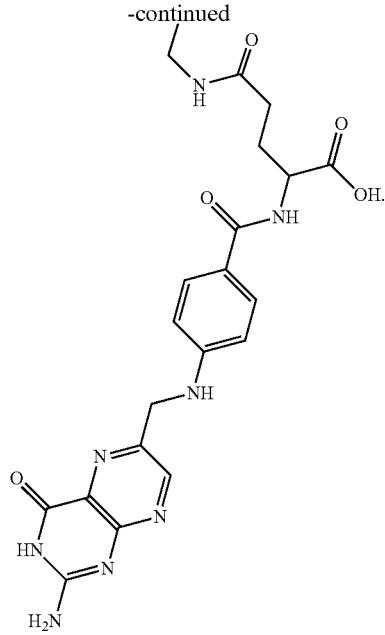
3. A pharmaceutical composition, comprising:
a chlorin e6-folic acid conjugate represented by the following Formula 1 or 2, or a pharmaceutically acceptable salt thereof:
[Formula 1]
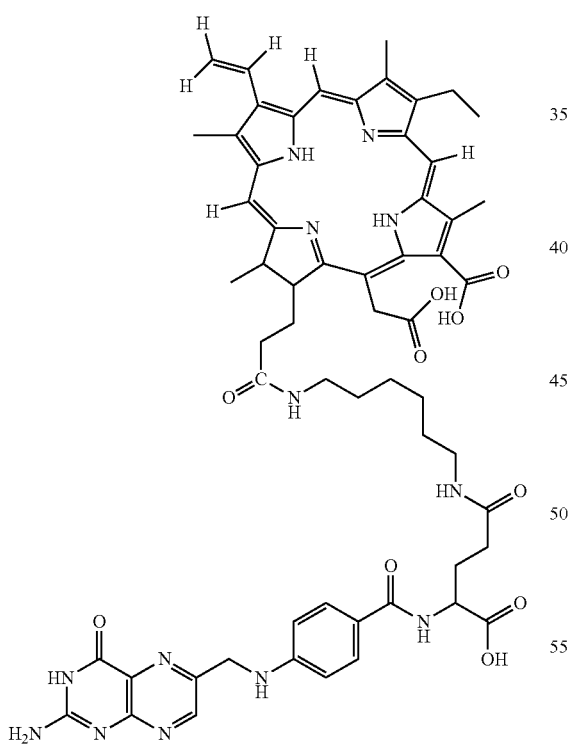
-continued
[Formula 2]
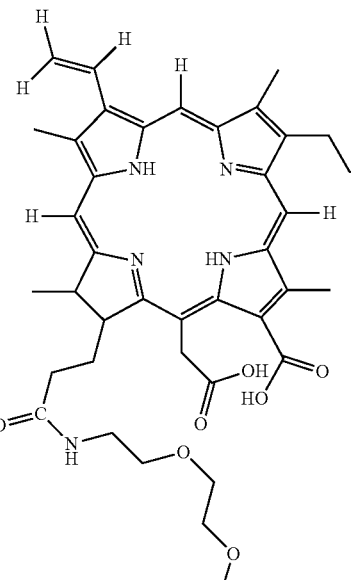
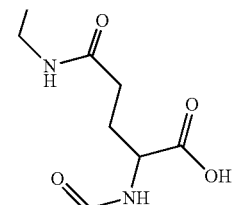
and a pharmaceutically acceptable carrier.
* * * * *